US009873745B2

(12) United States Patent
De Romeuf et al.

(10) Patent No.: US 9,873,745 B2
(45) Date of Patent: *Jan. 23, 2018

(54) ANTIBODY METHOD FOR TREATMENT OF A DISEASE IN WHICH THE TARGET CELLS ARE CELLS WHICH EXPRESS CD20

(71) Applicant: LABORATOIRE FRANCAIS DU FRACTIONNEMENT ET DES BIOTECHNOLOGIES, Les Ulis (FR)

(72) Inventors: Christophe De Romeuf, Lambersart (FR); Christine Gaucher, Sequedin (FR); Jean-Luc Teillaud, Paris (FR); Jean-Francois Prost, Versailles (FR)

(73) Assignee: LABORATOIRE FRANCAIS DU FRACTIONNEMENT ET DES BIOTECHNOLOGIES, Les Ulis (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/828,177

(22) Filed: Aug. 17, 2015

(65) Prior Publication Data
US 2016/0060350 A1 Mar. 3, 2016

Related U.S. Application Data

(63) Continuation of application No. 11/793,138, filed as application No. PCT/FR2005/003123 on Dec. 14, 2005, now Pat. No. 9,234,045.

(30) Foreign Application Priority Data
Dec. 15, 2004 (FR) ..................... 04 13320

(51) Int. Cl.
A61K 39/395 (2006.01)
C07K 16/28 (2006.01)
C07K 16/30 (2006.01)
A61K 51/10 (2006.01)
A61K 39/00 (2006.01)

(52) U.S. Cl.
CPC ...... *C07K 16/2887* (2013.01); *A61K 51/1069* (2013.01); *C07K 16/2896* (2013.01); *C07K 16/3061* (2013.01); *A61K 2039/505* (2013.01); *C07K 2317/24* (2013.01); *C07K 2317/56* (2013.01); *C07K 2317/76* (2013.01); *C12N 2510/02* (2013.01)

(58) Field of Classification Search
None
See application file for complete search history.

(56) References Cited

U.S. PATENT DOCUMENTS

| 2003/0133939 A1 | 7/2003 | Ledbetter et al. |
| 2004/0110704 A1 | 6/2004 | Yamane et al. |
| 2005/0249732 A1 | 11/2005 | de Romeuf et al. |
| 2005/0271652 A1 | 12/2005 | de Romeuf et al. |
| 2006/0127392 A1 | 6/2006 | de Romeuf et al. |
| 2008/0241103 A1 | 10/2008 | Qian |

FOREIGN PATENT DOCUMENTS

| WO | WO 98/41645 A1 | 9/1998 |
| WO | WO01/10460 A1 | 2/2001 |
| WO | WO 02/079255 A1 | 10/2002 |
| WO | WO 03/085107 A1 | 10/2003 |
| WO | WO 2004/024768 A2 | 3/2004 |
| WO | WO 2004/028564 A2 | 4/2004 |
| WO | WO 2004/029092 A2 | 4/2004 |
| WO | WO 2004/035607 A2 | 4/2004 |
| WO | WO 2004/056312 A2 | 7/2004 |
| WO | WO 2005/063815 A2 | 7/2005 |

OTHER PUBLICATIONS

Becker et al., "Rituximab as treatment for refractory kidney transplant rejection," Am J Transplant, 2004, vol. 4, pp. 996-1001.
Chaperot et al., "Differentiation of antigen-presenting cells (dendritic cells and macrophages) for therapeutic application in patients with lymphoma," Leukemia, 2000, vol. 14, No. 9, pp. 1667-1677.
De Pascalis et al., "Grafting of "Abbreviated" Complementarity Determining Regions Containing Specificity Determining Residues Essential for Ligand Contact to Engineer a Less Immunogenic Humanzied Monoclonal Antibody," Journal of Immunology, 2002. vol. 169, pp. 3076-3084.
Golay et al., "The CD20 (Bp35) antigen is involved in activation of B cells from the $G_0$ to the $G_1$ phase of the cell cycle," J Immunol, Dec. 1985, vol. 135, No. 6, pp. 3795-3801.
Grillo-Lopez et al., "IDEC-C2BB chimeric anti-CD20 antibody (MAB): safety and clinical activity in the treatment of patients (PTS) with relapsed low-grade or follicular (IWF :A-D) non-hodgkin's lymphoma (NHL)," British Journal of Haematology, vol. 93, 1996, p. 283.
Kimby et al., "Differences in blood T and NK cell populations between chronic lymphocytic leukemia of B cell type (B-CLL) and monoclonal B-lymphocytosis of undetermined significance (B-MLUS)," Leukemia, Jul. 1989, vol. 3, No. 7, pp. 501-504.
Liu et al., "Production of a mouse-human chimeric monoclonal antibody to CD20 with potent Fc-dependent biologic activity," The Journal of Immunology, Nov. 15, 1987, vol. 139, No. 10, pp. 3521-3526.
MacCallum et al., "Antibody-antigen Interactions: Contact Analysis and Binding Site Topography," Journal of Molecular Biology, 1996. vol. 262, pp. 732-745.

(Continued)

Primary Examiner — Ron Schwadron
(74) Attorney, Agent, or Firm — Birch, Stewart, Kolasch & Birch, LLP

(57) ABSTRACT

The present invention relates to a monoclonal antibody method directed against CD20 antigen including administration of an anti CD20 antibody wherein each of the light chains thereof has the murine-human chimeric amino acid sequence SEQ ID NO: 28, and each of the heavy chains thereof has the murine-human chimeric amino acid sequence SEQ ID NO: 20.

17 Claims, 10 Drawing Sheets

(56) References Cited

OTHER PUBLICATIONS

Mavromatis et al., "Monoclonal antibody therapy of chronic lymphocytic leukemia," J Clin Oncol, May 1, 2003, vol. 21, No. 9, pp. 1874-1881.
Mavromatis et al., "Novel therapies for chronic lymphocytic leukemia," Blood Rev, 2004, vol. 18, No. 2, pp. 137-148.
Moreton et al., "Alemtuzumab therapy in B-cell lymphoproliferative disorders," Semin Oncol. Aug. 2003, vol. 30, No. 4, pp. 493-501.
Morrison et al., "Chimeric human antibody molecules: mouse antigen-binding domains with human constant region domains," Proc Natl Acad Sci, Immunology, Nov. 1984, vol. 81, pp. 6851-6855.
Peller et al., "Decreased CD45RA T cells in B-cell chronic lymphatic leukemia patients: correlation with disease stage," Blood, Sep. 15, 1991 Sep, vol. 78, No. 6, pp. 1569-1573.
Platsoucas et al., "Abnormal T lymphocyte subpopulations in patients with B cell chronic lymphocytic leukemia: an analysis by monoclonal antibodies," J Immunol, Nov. 1982, vol. 129, No. 5, pp. 2305-2312.
Ratanatharathorn et al., "Treatment of chronic graft-versus-host disease with anti-CD20 chimeric monoclonal antibody," Biol Blood Marrow Transplant, 2003, vol. 9, pp. 505-511.
Rawstron et al., "Early prediction of outcome and response to alemtuzumab therapy in chronic lymphocvtic leukemia," Blood, Mar. 15, 2004, vol. 103, No. 6, pp. 2027-2031.
Robak, "Monoclonal antibodies in the treatment of chronic lymphoid leukemias," Leuk Lymphoma, Feb. 2004, vol. 45, No. 2, pp. 205-219.
Rudikoff et al., "Single amino acid substitution altering antigen-binding specificity," Proc. Natl. Acad. Sci, USA, Mar. 1982, Immunology, vol. 79, pp. 1979-1983.
Salvatore et al., "Improved cytotoxic activity toward cell lines and fresh leukemia cells of a mutant anti-CD22 immunotoxin obtained by antibody phage display," Clin Cancer Res, Apr. 2002, vol. 8, No. 4, pp. 995-1002.
Sørskaar et al., "Natural killer cells in chronic leukemia. Function and markers," Int Arch Allergy Appl Immunol, 1988, vol. 87, No. 2, pp. 159-164.
Stranglmaier et al., "Rituximab and alemtuzumab induce a nonclassic, caspas-independent apoptotic pathway in B-lymphoid cell lines and in chronic lymphocytic leukemia cells," Ann Hematol, Oct. 2004 (published online Aug. 7, 2004), vol. 83, No. 10, pp. 634-645.
Sun et al., "Late and Chronic Antibody-Mediated Rejection: Main Barrier to Long Term Graft Survival," Clinical and Developmental Immunology, vol. 2013, Article ID 859761, 7 pages., http://dx.doi.org/10.1155/2013/859761, retrieved Apr. 14, 2015.
Tedder et al., "Antibodies reactive with the B1 molecule inhibit cell cycle progression but not activation of human B lymphocytes," Eur J Immunol, 1986, vol. 16, No. 8, pp. 881-887.
Valentine et al., "Expression of the Human B-cell Surface Protein CD20: Alteration by Phorbol 12-myristate 13-acetate," Proc Natl Acad Sci, Nov. 1987, vol. 84, pp. 8085-8089.
Valentine et al., "Phosphorylation of the CD20 phosphoprotein in resting B lymphocytes," J Biol Chem, Jul. 5, 1989, vol. 284, No. 19, pp. 11282-11287.
Vuillier et al., "Cell therapy by dendritic cells in chronic lymphoid leukemia: state of the Art," Bull Cancer, 2003, vol. 90, No. 8-9, pp. 744-750, English abstract provided.
Ziegler et al., "Deficiency of natural killer cell activity in patients with chronic lymphocytic leukemia," Int J Cancer, 1981, vol. 27, No. 3, pp. 321-327.
Coleman et al., "Epratuzumab: targeting B-cell malignancies through CD221," Clin Cancer Res, Sep. 1, 2003, vol. 9, No. 10 (part 2), pp. 3991S-3994S.
Shinkawa et al., "The absence of fucose but not the presence of galactose or bisecting N-acetylglucosamine of human IgG1 complex-type oligosacchardies shows the cirtical role of enhancing antibody-dependent cellular cytotoxicity," J of Bio Chem, vol. 278, No. 5, Jan. 31, 2003, pp. 3466-73.
Teeling et al., "Characterization of new human CD20 monoclonal antibodies with potent cytolytic activity against non-Hodgkin lymphomas," Blood, vol. 104, No. 6, 2004, pp. 1793-1800.

SEQUENCE LISTING

<160> NUMBER OF SEQ ID NOS: 29

<210> SEQ ID NO 1
<211> LENGTH: 24
<212> TYPE: DNA
<213> ORGANISM: Artificial Sequence
<220> FEATURE:
<223> OTHER INFORMATION: Primer

<400> SEQUENCE: 1
actgccatca atcttccact tgac                                          24

<210> SEQ ID NO 2
<211> LENGTH: 23
<212> TYPE: DNA
<213> ORGANISM: Artificial Sequence
<220> FEATURE:
<223> OTHER INFORMATION: Primer

<400> SEQUENCE: 2
ctgagggtgt agaggtcaga ctg                                           23

<210> SEQ ID NO 3
<211> LENGTH: 28
<212> TYPE: DNA
<213> ORGANISM: Artificial Sequence
<220> FEATURE:
<223> OTHER INFORMATION: Primer

<400> SEQUENCE: 3
ttgttcaaga agcacacgac tgaggcac                                      28

<210> SEQ ID NO 4
<211> LENGTH: 28
<212> TYPE: DNA
<213> ORGANISM: Artificial Sequence
<220> FEATURE:
<223> OTHER INFORMATION: Primer

<400> SEQUENCE: 4
gagttccagg tcaaggtcac tggctcag                                      28

<210> SEQ ID NO 5

<211> LENGTH: 321
<212> TYPE: DNA
<213> ORGANISM: Mus musculus

<400> SEQUENCE: 5

```
caaattgttc tctcccagtc tccagcaatc ctgtctgcat ctccagggga gaaggtcaca    60
atgacttgca gggccagctc aagtgtaagt tacatgcact ggtaccagca gaagccagga   120
tcctccccca aaccctggat ttatgccaca tccaacctgg cttctggagt ccctgctcgc   180
ttcagtggca gtgggtctgg gacctcttat tctttcacaa tcagcagagt ggaggctgaa   240
gatgctgcca cttattactg ccagcagtgg acttttaacc cacccacgtt cggagggggg   300
accaggctgg aaataaaccg g                                             321
```

<210> SEQ ID NO 6
<211> LENGTH: 107
<212> TYPE: PRT
<213> ORGANISM: Mus musculus

<400> SEQUENCE: 6

```
Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Phe Thr Ile Ser Arg Val Glu Ala Glu
65                  70                  75                  80

Asp Ala Ala Thr Tyr Tyr Cys Gln Gln Trp Thr Phe Asn Pro Pro Thr
                85                  90                  95

Phe Gly Gly Gly Thr Arg Leu Glu Ile Asn Arg
            100                 105
```

<210> SEQ ID NO 7
<211> LENGTH: 354
<212> TYPE: DNA
<213> ORGANISM: Mus musculus

<400> SEQUENCE: 7

```
caggcttatc tacagcagtc tggggctgag ctggtgaggc ctggggcctc agtgaagatg    60
tcctgcaagg cttctggcta cacatttacc agttacaata tgcactgggt aaagcagaca   120
cctagacagg gcctggaatg gattggaggt atttatccag gaaatggtga tacttcctac   180
aatcagaagt tcaagggcaa ggccacactg actgtaggca atcctccag cacagcctac   240
atgcagctca gcagcctgac atctgaagac tctgcggtct atttctgtgc aagatatgac   300
tacaactatg ctatggacta ctgggtcaa ggaacctcag tcaccgtctc ctca           354
```

<210> SEQ ID NO 8
<211> LENGTH: 118
<212> TYPE: PRT
<213> ORGANISM: Mus musculus

<400> SEQUENCE: 8

```
Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser Tyr
```

```
                    20                  25                  30
Asn Met His Trp Val Lys Gln Thr Pro Arg Gln Gly Leu Glu Trp Ile
             35                  40                  45

Gly Gly Ile Tyr Pro Gly Asn Gly Asp Thr Ser Tyr Asn Gln Lys Phe
         50                  55                  60

Lys Gly Lys Ala Thr Leu Thr Val Gly Lys Ser Ser Ser Thr Ala Tyr
 65                  70                  75                  80

Met Gln Leu Ser Ser Leu Thr Ser Glu Asp Ser Ala Val Tyr Phe Cys
                 85                  90                  95

Ala Arg Tyr Asp Tyr Asn Tyr Ala Met Asp Tyr Trp Gly Gln Gly Thr
            100                 105                 110

Ser Val Thr Val Ser Ser
        115
```

<210> SEQ ID NO 9
<211> LENGTH: 47
<212> TYPE: DNA
<213> ORGANISM: Artificial Sequence
<220> FEATURE:
<223> OTHER INFORMATION: Primer

<400> SEQUENCE: 9
ctcagtacta gtgccgccac catggatttt caagtgcaga ttttcag      47

<210> SEQ ID NO 10
<211> LENGTH: 46
<212> TYPE: DNA
<213> ORGANISM: Artificial Sequence
<220> FEATURE:
<223> OTHER INFORMATION: Primer

<400> SEQUENCE: 10
tgaagacact tggtgcagcc acagtccggt ttatttccag cctggt       46

<210> SEQ ID NO 11
<211> LENGTH: 5289
<212> TYPE: DNA
<213> ORGANISM: Artificial Sequence
<220> FEATURE:
<223> OTHER INFORMATION: Vector

<400> SEQUENCE: 11
gatctcccga tccctatgg tgcactctca gtacaatctg ctctgatgcc gcatagttaa     60
gccagtatct gctccctgct tgtgtgttgg aggtcgctga gtagtgcgcg agcaaaattt   120
aagctacaac aaggcaaggc ttgaccgaca attgcatgaa gaatctgctt agggttaggc   180
gttttgcgct gcttcgcgat gtacgggcca gatatacgcg tatctgaggg gactagggtg   240
tgtttaggcg aaaagcgggg cttcggttgt acgcggttag gagtcccctc aggatatagt   300
agtttcgctt tgcataggg aggggaaat gtagtcttat gcaatactct tgtagtcttg   360
caacatggta acgatgagtt agcaacatgc cttacaagga gagaaaaagc accgtgcatg   420
ccgattggtg gaagtaaggt ggtacgatcg tgccttatta ggaaggcaac agacgggtct   480
gacatggatt ggacgaacca ctgaattccg cattgcagag atattgtatt taagtgccta   540
gctcgataca ataaacgcca tttgaccatt caccacattg gtgtgcacct ccaagcttgg   600
taccgagctc ggatccacta gtaacggccg ccagtgtgct ggaattctgc agatatccat   660
cacactggcg gccgctggct gcaccaagtg tcttcatctt cccgccatct gatgagcagt   720
tgaaatctgg aactgcctct gttgtgtgcc tgctgaataa cttctatccc agagaggcca   780

```
aagtacagtg gaaggtggat aacgccctcc aatcgggtaa ctcccaggag agtgtcacag    840
agcaggacag caaggacagc acctacagcc tcagcagcac cctgacgctg agcaaagcag    900
actacgagaa acacaaagtc tacgcctgcg aagtcaccca tcagggcctg agctcgcccg    960
tcacaaagag cttcaacagg ggagagtgtt agtctagagc tcgctgatca gcctcgactg   1020
tgccttctag ttgccagcca tctgttgttt gcccctcccc cgtgccttcc ttgaccctgg   1080
aaggtgccac tcccactgtc ctttcctaat aaaatgagga aattgcatcg cattgtctga   1140
gtaggtgtca ttctattctg ggggtgggg tggggcagga cagcaagggg gaggattggg   1200
aagacaatag caggcatgct ggggatgcgg tgggctctat ggcttctgag gcggaaagaa   1260
ccagctgggg ctcgactgtg gaatgtgtgt cagttagggt gtggaaagtc cccaggctcc   1320
ccagcaggca gaagtatgca aagcatgcat ctcaattagt cagcaaccag gtgtggaaag   1380
tccccaggct ccccagcagg cagaagtatg caaagcatgc atctcaatta gtcagcaacc   1440
atagtcccgc ccctaactcc gcccatcccg ccctaactc cgcccagttc cgcccattct   1500
ccgccccatg gctgactaat ttttttatt tatgcagagg ccgaggccgc ctcggcctct   1560
gagctattcc agaagtagtg aggaggcttt tttggaggcc taggcttttg caaaaagctt   1620 ggggggggg acagctcagg gctgcgattt cgcgccaaac ttgacggcaa tcctagcgtg   1680
aaggctggta ggattttatc cccgctgcca tcatggttcg accattgaac tgcatcgtcg   1740
ccgtgtccca agatatgggg attggcaaga acggagacct accctggcct ccgctcagga   1800
acgagttcaa gtacttccaa agaatgacca caacctcttc agtggaaggt aaacagaatc   1860
tggtgattat gggtaggaaa acctggttct ccattcctga gaagaatcga cctttaaagg   1920
acagaattaa tatagttctc agtagagaac tcaaagaacc accacgagga gctcattttc   1980
ttgccaaaag tttggatgat gccttaagac ttattgaaca accggaattg gcaagtaaag   2040
tagacatggt ttggatagtc ggaggcagtt ctgtttacca ggaagccatg aatcaaccag   2100
gccacctcag actctttgtg acaaggatca tgcaggaatt tgaaagtgac acgttttttcc   2160 cagaaattga tttggggaaa tataaacttc tcccagaata cccaggcgtc ctctctgagg   2220
tccaggagga aaaaggcatc aagtataagt ttgaagtcta cgagaagaaa gactaacagg   2280
aagatgcttt caagttctct gctcccctcc taaagctatg catttttata agaccatggg   2340
acttttgctg gctttagatc gatctttgtg aaggaacctt acttctgtgg tgtgacataa   2400
ttggacaaac tacctacaga gatttaaagc tctaaggtaa atataaaatt tttaagtgta   2460
taatgtgtta aactactgat tctaattgtt tgtgtatttt agattccaac ctatggaact   2520
gatgaatggg agcagtggtg gaatgccttt aatgaggaaa acctgttttg ctcagaagaa   2580
atgccatcta gtgatgatga ggctactgct gactctcaac attctactcc tccaaaaaag   2640
aagagaaagg tagaagaccc caaggacttt ccttcagaat tgctaagttt tttgagtcat   2700
gctgtgttta gtaatagaac tcttgcttgc tttgctattt acaccacaaa ggaaaaagct   2760
gcactgctat acaagaaaat tatggaaaaa tattctgtaa cctttataag taggcataac   2820
agttataatc ataacatact gttttttctt actccacaca ggcatagagt gtctgctatt   2880
aataactatg ctcaaaaatt gtgtaccttt agctttttaa tttgtaaagg ggttaataag   2940
gaatatttga tgtatagtgc cttgactaga gatcataatc agccatacca catttgtaga   3000
ggttttactt gctttaaaaa acctcccaca cctcccctg aacctgaaac ataaaatgaa   3060
tgcaattgtt gttgttaact tgtttattgc agcttataat ggttacaaat aaagcaatag   3120
```

```
catcacaaat ttcacaaata aagcattttt ttcactgcat tctagttgtg gtttgtccaa    3180
actcatcaat gtatcttatc atgtctggat ccgcgtatgg tgcactctca gtacaatctg    3240
ctctgatgcc gcatagttaa gccagccccg acacccgcca acacccgctg acgcgccctg    3300
acgggcttgt ctgctcccgg catccgctta cagacaagct gtgaccgtct ccgggagctg    3360
catgtgtcag aggttttcac cgtcatcacc gaaacgcgcg agacgaaagg gcctcgtgat    3420
acgcctattt ttataggtta atgtcatgat aataatggtt tcttagacgt caggtggcac    3480
ttttcgggga atgtgcgcg gaacccctat ttgtttattt ttctaaatac attcaaatat    3540
gtatccgctc atgagacaat aaccctgata aatgcttcaa taatattgaa aaaggaagag    3600
tatgagtatt caacatttcc gtgtcgccct tattccctt tttgcggcat tttgccttcc    3660
tgttttgct cacccagaaa cgctggtgaa agtaaaagat gctgaagatc agttgggtgc    3720
acgagtgggt tacatcgaac tggatctcaa cagcggtaag atccttgaga gttttcgccc    3780
cgaagaacgt tttccaatga tgagcacttt taaagttctg ctatgtggcg cggtattatc    3840
ccgtattgac gccgggcaag agcaactcgg tcgccgcata cactattctc agaatgactt    3900
ggttgagtac tcaccagtca cagaaaagca tcttacggat ggcatgacag taagagaatt    3960
atgcagtgct gccataacca tgagtgataa cactgcggcc aacttacttc tgacaacgat    4020
cggaggaccg aaggagctaa ccgcttttt gcacaacatg ggggatcatg taactcgcct    4080
tgatcgttgg gaaccggagc tgaatgaagc cataccaaac gacgagcgtg acaccacgat    4140
gcctgtagca atggcaacaa cgttgcgcaa actattaact ggcgaactac ttactctagc    4200
ttcccggcaa caattaatag actggatgga ggcggataaa gttgcaggac cacttctgcg    4260
ctcggccctt ccggctggct ggtttattgc tgataaatct ggagccggtg agcgtgggtc    4320
tcgcggtatc attgcagcac tggggccaga tggtaagccc tcccgtatcg tagttatcta    4380
cacgacgggg agtcaggcaa ctatggatga acgaaataga cagatcgctg agataggtgc    4440
ctcactgatt aagcattggt aactgtcaga ccaagtttac tcatatatac tttagattga    4500
tttaaaactt catttttaat ttaaaaggat ctaggtgaag atcctttttg ataatctcat    4560
gaccaaaatc ccttaacgtg agttttcgtt ccactgagcg tcagaccccg tagaaaagat    4620
caaaggatct cttgagatc ctttttttct gcgcgtaatc tgctgcttgc aaacaaaaaa    4680
accaccgcta ccagcggtgg tttgtttgcc ggatcaagag ctaccaactc tttttccgaa    4740
ggtaactggc ttcagcagag cgcagatacc aaatactgtc cttctagtgt agccgtagtt    4800
aggccaccac ttcaagaact ctgtagcacc gcctacatac ctcgctctgc taatcctgtt    4860
accagtggct gctgccagtg gcgataagtc gtgtcttacc gggttggact caagacgata    4920
gttaccggat aaggcgcagc ggtcgggctg aacggggggt tcgtgcacac agcccagctt    4980
ggagcgaacg acctacaccg aactgagata cctacagcgt gagctatgag aaagcgccac    5040
gcttcccgaa gggagaaagg cggacaggta tccggtaagc ggcagggtcg gaacaggaga    5100
gcgcacgagg gagcttccag ggggaaacgc ctggtatctt tatagtcctg tcgggtttcg    5160
ccacctctga cttgagcgtc gatttttgtg atgctcgtca ggggggcgga gcctatggaa    5220
aaacgccagc aacgcggcct ttttacggtt cctggccttt tgctggcctt ttgctcacat    5280
ggctcgaca                                                             5289
```

<210> SEQ ID NO 12  
<211> LENGTH: 6275  
<212> TYPE: DNA  
<213> ORGANISM: Artificial Sequence
<220> FEATURE:
<223> OTHER INFORMATION: Vector

<400> SEQUENCE: 12

| | | | | | |
|---|---|---|---|---|---|
| tcgaggagac | ctgcaaagat | ggataaagtt | ttaaacagag | aggaatcttt | gcagctaatg | 60 |
| gaccttctag | gtcttgaaag | gagtgggaat | tggctccggt | gcccgtcagt | gggcagagcg | 120 |
| cacatcgccc | acagtccccg | agaagttgtg | gggaggggtc | ggcaattgaa | ccggtgccta | 180 |
| gagaaggtgg | cgcggggtaa | actgggaaag | tgatgtcgtg | tactggctcc | gccttttcc | 240 |
| cgagggtggg | ggagaaccgt | atataagtgc | agtagtcgcc | gtgaacgttc | ttttcgcaa | 300 |
| cgggtttgcc | gccagaacac | aggtaagtgc | cgtgtgtggt | tcccgcgggc | ctggcctctt | 360 |
| tacgggttat | ggcccttgcg | tgccttgaat | tacttccacc | tggctgcagt | acgtgattct | 420 |
| tgatcccgag | cttcggggttg | gaagtgggtg | ggagagttcg | aggccttgcg | cttaaggagc | 480 |
| cccttcgcct | cgtgcttgag | ttgaggcctg | gcctgggcgc | tggggccgcc | gcgtgcgaat | 540 |
| ctggtggcac | cttcgcgcct | gtctcgctgc | tttcgataag | tctctagcca | tttaaaattt | 600 |
| ttgatgacct | gctgcgacgc | ttttttttctg | gcaagatagt | cttgtaaatg | cgggccaaga | 660 |
| tctgcacact | ggtatttcgg | ttttggggc | cgcgggcggc | gacggggccc | gtgcgtccca | 720 |
| gcgcacatgt | tcggcgaggc | ggggcctgcg | agcgcggcca | ccgagaatcg | gacggggta | 780 |
| gtctcaagct | ggccggcctg | ctctggtgcc | tggcctcgcg | ccgccgtgta | tcgcccccgcc | 840 |
| ctgggcggca | aggctggccc | ggtcggcacc | agttgcgtga | gcggaaagat | ggccgcttcc | 900 |
| cggccctgct | gcagggagct | caaaatggag | gacgcggcgc | tcgggagagc | gggcgggtga | 960 |
| gtcacccaca | caaaggaaaa | gggcctttcc | gtcctcagcc | gtcgcttcat | gtgactccac | 1020 |
| ggagtaccgg | gcgccgtcca | ggcacctcga | ttagttctcg | agcttttgga | gtacgtcgtc | 1080 |
| tttaggttgg | ggggaggggt | tttatgcgat | ggagttttccc | cacactgagt | gggtggagac | 1140 |
| tgaagttagg | ccagcttggc | acttgatgta | attctccttg | gaatttgccc | ttttttgagtt | 1200 |
| tggatcttgg | ttcattctca | agcctcagac | agtggttcaa | agtttttttc | ttccatttca | 1260 |
| ggtgtcgtga | ggaattagct | tggtacaaac | agcaaagctt | aaggtactag | tgccgccacc | 1320 |
| atggattttc | aagtgcagat | tttcagcttc | ctgctaatca | gtgcttcagt | cataatgtcc | 1380 |
| agaggacaaa | ttgttctctc | ccagtctcca | gcaatcctgt | ctgcatctcc | aggggagaag | 1440 |
| gtcacaatga | cttgcagggc | cagctcaagt | gtaagttaca | tgcactggta | ccagcagaag | 1500 |
| ccaggatcct | cccccaaacc | ctggatttat | gccacatcca | acctggcttc | tggagtccct | 1560 |
| gctcgcttca | gtggcagtgg | gtctgggacc | tcttattctt | tcacaatcag | cagagtggag | 1620 |
| gctgaagatg | ctgccactta | ttactgccag | cagtggactt | taacccacc | cacgttcgga | 1680 |
| ggggggacca | ggctggaaat | aaaccggact | gtggctgcac | caagtgtctt | catcttcccg | 1740 |
| ccatctgatg | agcagttgaa | atctggaact | gcctctgttg | tgtgcctgct | gaataacttc | 1800 |
| tatcccagag | aggccaaagt | acagtggaag | gtggataacg | ccctccaatc | gggtaactcc | 1860 |
| caggagagtg | tcacagagca | ggacagcaag | gacagcacct | acagcctcag | cagcaccctg | 1920 |
| acgctgagca | aagcagacta | cgagaaacac | aaagtctacg | cctgcgaagt | cacccatcag | 1980 |
| ggcctgagct | cgcccgtcac | aaagagcttc | aacagggag | agtgttagtc | tagagctcgc | 2040 |
| tgatcagcct | cgactgtgcc | ttctagttgc | cagccatctg | ttgtttgccc | ctccccgtg | 2100 |
| ccttccttga | ccctggaagg | tgccactccc | actgtccttt | cctaataaaa | tgaggaaatt | 2160 |
| gcatcgcatt | gtctgagtag | gtgtcattct | attctggggg | gtggggtggg | gcaggacagc | 2220 |

```
aaggggggagg attgggaaga caatagcagg catgctgggg atgcggtggg ctctatggct    2280
tctgaggcgg aaagaaccag ctggggctcg actgtggaat gtgtgtcagt tagggtgtgg    2340
aaagtcccca ggctccccag caggcagaag tatgcaaagc atgcatctca attagtcagc    2400
aaccaggtgt ggaaagtccc caggctcccc agcaggcaga agtatgcaaa gcatgcatct    2460
caattagtca gcaaccatag tcccgcccct aactccgccc atcccgcccc taactccgcc    2520
cagttccgcc cattctccgc cccatggctg actaattttt tttatttatg cagaggccga    2580
ggccgcctcg gcctctgagc tattccagaa gtagtgagga ggcttttttg gaggcctagg    2640
cttttgcaaa aagctttatc cccgctgcca tcatggttcg accattgaac tgcatcgtcg    2700
ccgtgtccca agatatgggg attggcaaga acggagacct accctggcct ccgctcagga    2760
acgagttcaa gtacttccaa agaatgacca caacctcttc agtggaaggt aaacagaatc    2820
tggtgattat gggtaggaaa acctggttct ccattcctga gaagaatcga cctttaaagg    2880
acagaattaa tatagttctc agtagagaac tcaaagaacc accacgagga gctcattttc    2940
ttgccaaaag tttggatgat gccttaagac ttattgaaca accggaattg gcaagtaaag    3000
tagacatggt ttggatagtc ggaggcagtt ctgtttacca ggaagccatg aatcaaccag    3060
gccacctcag actctttgtg acaaggatca tgcaggaatt tgaaagtgac acgttttttcc   3120 cagaaattga tttggggaaa tataaacttc tcccagaata cccaggcgtc ctctctgagg    3180
tccaggagga aaaaggcatc aagtataagt ttgaagtcta cgagaagaaa gactaacagg    3240
aagatgcttt caagttctct gctcccctcc taaagctatg cattttttata agaccatggg   3300 acttttgctg gctttagatc gatctttgtg aaggaacctt acttctgtgg tgtgacataa    3360
ttggacaaac tacctacaga gatttaaagc tctaaggtaa atataaaatt tttaagtgta    3420
taatgtgtta aactactgat tctaattgtt tgtgtatttt agattccaac ctatggaact    3480
gatgaatggg agcagtggtg gaatgccttt aatgaggaaa acctgttttg ctcagaagaa    3540
atgccatcta gtgatgatga ggctactgct gactctcaac attctactcc tccaaaaaag    3600
aagagaaagg tagaagaccc caaggacttt ccttcagaat tgctaagttt tttgagtcat    3660
gctgtgttta gtaatagaac tcttgcttgc tttgctattt acaccacaaa ggaaaaagct    3720
gcactgctat acaagaaaat tatggaaaaa tattctgtaa cctttataag taggcataac    3780
agttataatc ataacatact gttttttctt actccacaca ggcatagagt gtctgctatt    3840
aataactatg ctcaaaaatt gtgtaccttt agcttttta tttgtaaagg ggttaataag    3900
gaatatttga tgtatagtgc cttgactaga gatcataatc agccatacca catttgtaga    3960
ggttttactt gctttaaaaa acctcccaca cctcccctg aacctgaaac ataaaatgaa    4020
tgcaattgtt gttgttaact tgtttattgc agcttataat ggttacaaat aaagcaatag    4080
catcacaaat ttcacaaata aagcattttt tcactgcat tctagttgtg gtttgtccaa    4140
actcatcaat gtatcttatc atgtctggat ccgcgtatgg tgcactctca gtacaatctg    4200
ctctgatgcc gcatagttaa gccagccccg acacccgcca cacccgctg acgcgccctg    4260 acgggcttgt ctgctcccgg catccgctta cagacaagct gtgaccgtct ccgggagctg    4320
catgtgtcag aggttttcac cgtcatcacc gaaacgcgcg agacgaaagg gcctcgtgat    4380
acgcctattt ttataggtta atgtcatgat aataatggtt tcttagacgt caggtggcac    4440
ttttcgggga aatgtgcgcg gaacccctat ttgtttattt ttctaaatac attcaaatat    4500
gtatccgctc atgagacaat aaccctgata aatgcttcaa taatattgaa aaaggaagag    4560
tatgagtatt caacatttcc gtgtcgccct tattcccttt tttgcggcat tttgccttcc    4620
```

```
tgtttttgct cacccagaaa cgctggtgaa agtaaaagat gctgaagatc agttgggtgc    4680
acgagtgggt tacatcgaac tggatctcaa cagcggtaag atccttgaga gttttcgccc    4740
cgaagaacgt tttccaatga tgagcacttt taaagttctg ctatgtggcg cggtattatc    4800
ccgtattgac gccgggcaag agcaactcgg tcgccgcata cactattctc agaatgactt    4860
ggttgagtac tcaccagtca cagaaaagca tcttacggat ggcatgacag taagagaatt    4920
atgcagtgct gccataacca tgagtgataa cactgcggcc aacttacttc tgacaacgat    4980
cggaggaccg aaggagctaa ccgcttttttt gcacaacatg ggggatcatg taactcgcct    5040
tgatcgttgg gaaccggagc tgaatgaagc cataccaaac gacgagcgtg acaccacgat    5100
gcctgtagca atggcaacaa cgttgcgcaa actattaact ggcgaactac ttactctagc    5160
ttcccggcaa caattaatag actggatgga ggcggataaa gttgcaggac cacttctgcg    5220
ctcggccctt ccggctggct ggtttattgc tgataaatct ggagccggtg agcgtgggtc    5280
tcgcggtatc attgcagcac tggggccaga tggtaagccc tcccgtatcg tagttatcta    5340
cacgacgggg agtcaggcaa ctatggatga acgaaataga cagatcgctg agataggtgc    5400
ctcactgatt aagcattggt aactgtcaga ccaagtttac tcatatatac tttagattga    5460
tttaaaactt cattttttaat ttaaaaggat ctaggtgaag atcctttttg ataatctcat    5520
gaccaaaatc ccttaacgtg agttttcgtt ccactgagcg tcagacccccg tagaaaagat    5580 caaaggatct tcttgagatc ctttttttct gcgcgtaatc tgctgcttgc aaacaaaaaa    5640
accaccgcta ccagcggtgg tttgtttgcc ggatcaagag ctaccaactc ttttttccgaa    5700 ggtaactggc ttcagcagag cgcagatacc aaatactgtc cttctagtgt agccgtagtt    5760
aggccaccac ttcaagaact ctgtagcacc gcctacatac ctcgctctgc taatcctgtt    5820
accagtggct gctgccagtg gcgataagtc gtgtcttacc gggttggact caagacgata    5880
gttaccggat aaggcgcagc ggtcgggctg aacggggggt tcgtgcacac agcccagctt    5940
ggagcgaacg acctacaccg aactgagata cctacagcgt gagctatgag aaagcgccac    6000
gcttcccgaa gggagaaagg cggacaggta tccggtaagc ggcagggtcg gaacaggaga    6060
gcgcacgagg gagcttccag ggggaaacgc ctggtatctt tatagtcctg tcgggtttcg    6120
ccacctctga cttgagcgtc gatttttgtg atgctcgtca ggggggcgga gcctatggaa    6180
aaacgccagc aacgcggcct ttttacggtt cctggccttt tgctggcctt ttgctcacat    6240
ggctcgacag atccgacgga tcgggagatc ctagc                               6275
```

<210> SEQ ID NO 13
<211> LENGTH: 639
<212> TYPE: DNA
<213> ORGANISM: Artificial Sequence
<220> FEATURE:
<223> OTHER INFORMATION: Synthetic Construct

<400> SEQUENCE: 13

```
caaattgttc tctcccagtc tccagcaatc ctgtctgcat ctccagggga aaggtcaca      60 atgacttgca gggccagctc aagtgtaagt tacatgcact ggtaccagca gaagccagga    120
tcctccccca aaccctggat ttatgccaca tccaacctgg cttctggagt ccctgctcgc    180
ttcagtggca gtgggtctgg gacctcttat tctttcacaa tcagcagagt ggaggctgaa    240
gatgctgcca cttattactg ccagcagtgg acttttaacc cacccacgtt cggaggggg     300 accaggctgg aaataaaccg gactgtggct gcaccaagtg tcttcatctt cccgccatct    360
```

```
gatgagcagt tgaaatctgg aactgcctct gttgtgtgcc tgctgaataa cttctatccc    420
agagaggcca agtacagtg gaaggtggat aacgccctcc aatcgggtaa ctcccaggag     480
agtgtcacag agcaggacag caaggacagc acctacagcc tcagcagcac cctgacgctg    540
agcaaagcag actacgagaa acacaaagtc tacgcctgcg aagtcaccca tcagggcctg    600
agctcgcccg tcacaaagag cttcaacagg ggagagtgt                          639
```

```
<210> SEQ ID NO 14
<211> LENGTH: 213
<212> TYPE: PRT
<213> ORGANISM: Artificial Sequence
<220> FEATURE:
<223> OTHER INFORMATION: Synthetic Construct

<400> SEQUENCE: 14

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Val Ser Tyr Met
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Phe Thr Ile Ser Arg Val Glu Ala Glu
65                  70                  75                  80

Asp Ala Ala Thr Tyr Tyr Cys Gln Gln Trp Thr Phe Asn Pro Pro Thr
                85                  90                  95

Phe Gly Gly Gly Thr Arg Leu Glu Ile Asn Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

```
<210> SEQ ID NO 15
<211> LENGTH: 45
<212> TYPE: DNA
<213> ORGANISM: Artificial Sequence
<220> FEATURE:
<223> OTHER INFORMATION: Primer

<400> SEQUENCE: 15
ctcagtacta gtgccgccac catgggattc agcaggatct ttctc                    45

<210> SEQ ID NO 16
<211> LENGTH: 48
<212> TYPE: DNA
<213> ORGANISM: Artificial Sequence
```

```
<220> FEATURE:
<223> OTHER INFORMATION: Primer

<400> SEQUENCE: 16
gaccgatggg cccttggtgg aggctgagga gacggtgact gaggttcc         48

<210> SEQ ID NO 17
<211> LENGTH: 5739
<212> TYPE: DNA
<213> ORGANISM: Artificial Sequence
<220> FEATURE:
<223> OTHER INFORMATION: Vector

<400> SEQUENCE: 17
catggctcga cagatctccc gatcccctat ggtgcactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgtatctgag    240
gggactaggg tgtgtttagg cgaaaagcgg gcttcggtt gtacgcggtt aggagtcccc     300
tcaggatata gtagtttcgc ttttgcatag ggaggggggaa atgtagtctt atgcaatact    360
cttgtagtct tgcaacatgg taacgatgag ttagcaacat gccttacaag gagagaaaaa    420
gcaccgtgca tgccgattgg tggaagtaag gtggtacgat cgtgccttat taggaaggca    480
acagacgggt ctgacatgga ttggacgaac cactgaattc gcattgcag atattgta      540 tttaagtgcc tagctcgata caataaacgc catttgacca ttcaccacat tggtgtgcac    600
ctccaagctt ggtaccgagc tcggatccac tagtaacggc cgccagtgtg ctggaattct    660
gcagatatcc atcacactgg cggccgctcc accaagggcc catcggtctt cccctctggca    720 ccctcctcca agagcacctc tgggggcaca gcggccctgg gctgcctggt caaggactac    780
ttccccgaac cggtgacggt gtcgtggaac tcaggcgccc tgaccagcgg cgtgcacacc    840
ttcccggctg tcctacagtc ctcaggactc tactccctca gcagcgtggt gaccgtgccc    900
tccagcagct gggcaccca gacctacatc tgcaacgtga atcacaagcc cagcaacacc    960
aaggtggaca agaaagttga gcccaaatct tgtgacaaaa ctcacacatg cccaccgtgc    1020
ccagcacctg aactcctggg gggaccgtca gtcttcctct tccccccaaa acccaaggac    1080
accctcatga tctcccggac ccctgaggtc acatgcgtgg tggtggacgt gagccacgaa    1140
gaccctgagg tcaagttcaa ctggtacgtg gacggcgtgg aggtgcataa tgccaagaca    1200
aagccgcggg aggagcagta caacagcacg taccgtgtgg tcagcgtcct caccgtcctg    1260
caccaggact ggctgaatgg caaggagtac aagtgcaagg tctccaacaa agccctccca    1320
gcccccatcg agaaaaccat ctccaaagcc aaagggcagc ccgagaacc acaggtgtac    1380 accctgcccc catcccggga tgagctgacc aagaaccagg tcagcctgac ctgcctggtc    1440
aaaggcttct atcccagcga catcgccgtg gagtgggaga gcaatgggca gccggagaac    1500
aactacaaga ccacgcctcc cgtgctggac tccgacggct ccttcttcct ctacagcaag    1560
ctcaccgtgg acaagagcag gtggcagcag gggaacgtct tctcatgctc cgtgatgcat    1620
gaggctctgc acaaccacta cacgcagaag agcctctccc tgtctccggg taaatagtct    1680
agagctcgct gatcagcctc gactgtgcct tctagttgcc agccatctgt tgtttgcccc    1740
tcccccgtgc cttccttgac cctggaaggt gccactccca ctgtcctttc ctaataaaat    1800
gaggaaattg catcgcattg tctgagtagg tgtcattcta ttctgggggg tggggtgggg    1860
```

```
caggacagca agggggagga ttgggaagac aatagcaggc atgctgggga tgcggtgggc    1920
tctatggctt ctgaggcgga aagaaccagc tggggctcga gcgtgggcca tcgccctgat    1980
agacggtttt tcgcccttg acgttggagt ccacgttctt aatagtgga ctcttgttcc     2040 aaactggaac aacactcaac cctatctcgg tctattcttt tgatttataa gggattttgc    2100
cgatttcggc ctattggtta aaaatgagc tgatttaaca aatatttaac gcgaatttta    2160
acaaaatatt aacgtttaca atttcgcctg atgcggtatt ttctccttac gcatctgtgc    2220
ggtatttcac accgcatacg cggatctgcg cagcaccatg gcctgaaata acctctgaaa    2280
gaggaacttg gttaggtacc ttctgaggcg aaagaaccaa gctgtggaat gtgtgtcagt    2340
tagggtgtgg aaagtcccca ggctccccag caggcagaag tatgcaaagc atgcatctca    2400
attagtcagc aaccaggtgt ggaaagtccc caggctcccc agcaggcaga agtatgcaaa    2460
gcatgcatct caattagtca gcaaccatag tcccgcccct aactccgccc atcccgcccc    2520
taactccgcc cagttccgcc cattctccgc cccatggctg actaattttt tttatttatg    2580
cagaggccga ggccgcctcg gcctctgagc tattccagaa gtagtgagga gcttttttg    2640 gaggcctagg cttttgcaaa aagcttgatt cttctgacac aacagtctcg aacttaaggc    2700
tagagccacc atgattgaac aagatggatt gcacgcaggt tctccggccg cttgggtgga    2760
gaggctattc ggctatgact gggcacaaca gacaatcggc tgctctgatg ccgccgtgtt    2820
ccggctgtca gcgcaggggc gcccggttct ttttgtcaag accgacctgt ccggtgccct    2880
gaatgaactg caggacgagg cagcgcggct atcgtggctg gccacgacgg gcgttccttg    2940
cgcagctgtg ctcgacgttg tcactgaagc gggaagggac tggctgctat tgggcgaagt    3000
gccggggcag gatctcctgt catctcacct tgctcctgcc gagaaagtat ccatcatggc    3060
tgatgcaatg cggcggctgc atacgcttga tccggctacc tgcccattcg accaccaagc    3120
gaaacatcgc atcgagcgag cacgtactcg gatggaagcc ggtcttgtcg atcaggatga    3180
tctggacgaa gagcatcagg ggctcgcgcc agccgaactg ttcgccaggc tcaaggcgcg    3240
catgcccgac ggcgaggatc tcgtcgtgac ccatggcgat gcctgcttgc cgaatatcat    3300
ggtggaaaat ggccgctttt ctggattcat cgactgtggc cggctgggtg tggcggaccg    3360
ctatcaggac atagcgttgg ctacccgtga tattgctgaa gagcttggcg gcgaatgggc    3420
tgaccgcttc ctcgtgcttt acggtatcgc cgctcccgat tcgcagcgca tcgccttcta    3480
tcgccttctt gacgagttct tctgagcggg actctggggt tcgaaatgac cgaccaagcg    3540
acgcccaacc tgccatcacg atggccgcaa taaaatatct ttattttcat tacatctgtg    3600
tgttggtttt ttgtgtgaat cgatagcgat aaggatcgat cctctagcta gagtcgatcg    3660
acctgcaggg atccgcgtat ggtgcactct cagtacaatc tgctctgatg ccgcatagtt    3720
aagccagccc cgacacccgc caacacccgc tgacgcgccc tgacgggctt gtctgctccc    3780
ggcatccgct tacagacaag ctgtgaccgt ctccgggagc tgcatgtgtc agaggttttc    3840
accgtcatca ccgaaacgcg cgagacgaaa gggcctcgtg atacgcctat ttttataggt    3900
taatgtcatg ataataatgg tttcttagac gtcaggtggc acttttcggg gaaatgtgcg    3960
cggaacccct atttgtttat ttttctaaat acattcaaat atgtatccgc tcatgagaca    4020
ataaccctga taaatgcttc aataatattg aaaaaggaag agtatgagta ttcaacattt    4080
ccgtgtcgcc cttattccct ttttgcggc attttgcctt cctgtttttg ctcacccaga    4140
aacgctggtg aaagtaaaag atgctgaaga tcagttgggt gcacgagtgg gttacatcga    4200
actggatctc aacagcggta agatccttga gagttttcgc cccgaagaac gttttccaat    4260
```

```
gatgagcact tttaaagttc tgctatgtgg cgcggtatta tcccgtattg acgccgggca   4320
agagcaactc ggtcgccgca tacactattc tcagaatgac ttggttgagt actcaccagt   4380
cacagaaaag catcttacgg atggcatgac agtaagagaa ttatgcagtg ctgccataac   4440
catgagtgat aacactgcgg ccaacttact tctgacaacg atcggaggac cgaaggagct   4500
aaccgctttt ttgcacaaca tgggggatca tgtaactcgc cttgatcgtt gggaaccgga   4560
gctgaatgaa gccataccaa acgacgagcg tgacaccacg atgcctgtag caatggcaac   4620
aacgttgcgc aaactattaa ctggcgaact acttactcta gcttcccggc aacaattaat   4680
agactggatg gaggcggata agttgcagg accacttctg cgctcggccc ttccggctgg   4740
ctggtttatt gctgataaat ctggagccgg tgagcgtggg tctcgcggta tcattgcagc   4800
actggggcca gatggtaagc cctcccgtat cgtagttatc tacacgacgg ggagtcaggc   4860
aactatggat gaacgaaata gacagatcgc tgagataggt gcctcactga ttaagcattg   4920
gtaactgtca gaccaagttt actcatatat actttagatt gatttaaaac ttcatttta   4980 atttaaaagg atctaggtga agatccttt tgataatctc atgaccaaaa tcccttaacg   5040
tgagttttcg ttccactgag cgtcagaccc cgtagaaaag atcaaaggat cttcttgaga   5100 tcctttttt ctgcgcgtaa tctgctgctt gcaaacaaaa aaccaccgc taccagcggt   5160 ggtttgtttg ccggatcaag agctaccaac tctttttccg aaggtaactg gcttcagcag   5220
agcgcagata ccaaatactg tccttctagt gtagccgtag ttaggccacc acttcaagaa   5280
ctctgtagca ccgcctacat acctcgctct gctaatcctg ttaccagtgg ctgctgccag   5340
tggcgataag tcgtgtctta ccgggttgga ctcaagacga tagttaccgg ataaggcgca   5400
gcggtcgggc tgaacggggg gttcgtgcac acagcccagc ttggagcgaa cgacctacac   5460
cgaactgaga tacctacagc gtgagctatg agaaagcgcc acgcttcccg aagggagaaa   5520
ggcggacagg tatccggtaa gcggcagggt cggaacagga gagcgcacga gggagcttcc   5580
agggggaaac gcctggtatc tttatagtcc tgtcgggttt cgccacctct gacttgagcg   5640
tcgatttttg tgatgctcgt caggggggcg gagcctatgg aaaaacgcca gcaacgcggc   5700
ctttttacgg ttcctggcct tttgctggcc ttttgctca                           5739
```

<210> SEQ ID NO 18
<211> LENGTH: 6824
<212> TYPE: DNA
<213> ORGANISM: Artificial Sequence
<220> FEATURE:
<223> OTHER INFORMATION: Vector

<400> SEQUENCE: 18

```
tcgaggagac ctgcaaagat ggataaagtt ttaaacagag aggaatcttt gcagctaatg    60
gaccttctag gtcttgaaag gagtgggaat tggctccggt gcccgtcagt gggcagagcg   120
cacatcgccc acagtcccg agaagttgtg gggaggggtc ggcaattgaa ccggtgccta   180
gagaaggtgg cgcggggtaa actgggaaag tgatgtcgtg tactggctcc gccttttcc   240 cgagggtggg ggagaaccgt atataagtgc agtagtcgcc gtgaacgttc ttttcgcaa   300 cgggtttgcc gccagaacac aggtaagtgc cgtgtgtggt tcccgcgggc ctggcctctt   360
tacgggttat ggcccttgcg tgccttgaat tacttccacc tggctgcagt acgtgattct   420
tgatcccgag cttcggggttg gaagtgggtg ggagagttcg aggccttgcg cttaaggagc   480
cccttcgcct cgtgcttgag ttgaggcctg gcctgggcgc tggggccgcc gcgtgcgaat   540
```

```
ctggtggcac cttcgcgcct gtctcgctgc tttcgataag tctctagcca tttaaaattt    600
ttgatgacct gctgcgacgc ttttttttctg gcaagatagt cttgtaaatg cgggccaaga   660
tctgcacact ggtatttcgg ttttttgggc cgcgggcggc gacggggccc gtgcgtccca    720
gcgcacatgt tcggcgaggc ggggcctgcg agcgcggcca ccgagaatcg gacgggggta    780
gtctcaagct ggccggcctg ctctggtgcc tggcctcgcg ccgccgtgta tcgcccgcc    840
ctgggcggca aggctggccc ggtcggcacc agttgcgtga gcggaaagat ggccgcttcc    900
cggccctgct gcagggagct caaaatggag gacgcggcgc tcgggagagc gggcgggtga    960
gtcacccaca caaaggaaaa gggccttttcc gtcctcagcc gtcgcttcat gtgactccac   1020
ggagtaccgg gcgccgtcca ggcacctcga ttagttctcg agcttttgga gtacgtcgtc    1080
tttaggttgg gggagggggt tttatgcgat ggagtttccc cacactgagt gggtggagac    1140
tgaagttagg ccagcttggc acttgatgta attctccttg gaatttgccc tttttgagtt    1200
tggatcttgg ttcattctca agcctcagac agtggttcaa agttttttc ttccatttca    1260
ggtgtcgtga ggaattagct tggtacaaac agcaaagctt aaggtactag tgccgccacc   1320
atgggattca gcaggatctt tctcttcctc ctgtcagtaa ctacaggtgt ccactcccag    1380
gcttatctac agcagtctgg ggctgagctg gtgaggcctg gggcctcagt gaagatgtcc    1440
tgcaaggctt ctggctacac atttaccagt tacaatatgc actgggtaaa gcagacacct    1500
agacagggcc tggaatggat tggaggtatt tatccaggaa atggtgatac ttcctacaat    1560
cagaagttca agggcaaggc cacactgact gtaggcaaat cctccagcac agcctacatg    1620
cagctcagca gcctgacatc tgaagactct gcggtctatt tctgtgcaag atatgactac    1680
aactatgcta tggactactg gggtcaagga acctcagtca ccgtctcctc agcctccacc    1740
aagggcccat cggtcttccc cctggcaccc tcctccaaga gcacctctgg gggcacagcg    1800
gccctgggct gcctggtcaa ggactacttc cccgaaccgg tgacggtgtc gtggaactca    1860
ggcgccctga ccagcggcgt gcacaccttc ccggctgtcc tacagtcctc aggactctac    1920
tccctcagca gcgtggtgac cgtgccctcc agcagcttgg gcacccagac ctacatctgc    1980
aacgtgaatc acaagcccag caacaccaag gtggacaaga agttgagccc caaatcttgt    2040
gacaaaactc acacatgccc accgtgccca gcacctgaac tcctgggggg accgtcagtc    2100
ttcctcttcc ccccaaaacc caaggacacc ctcatgatct cccggacccc tgaggtcaca    2160
tgcgtggtgg tggacgtgag ccacgaagac cctgaggtca agttcaactg gtacgtggac    2220
ggcgtggagg tgcataatgc caagacaaag ccgcgggagg agcagtacaa cagcacgtac    2280
cgtgtggtca gcgtcctcac cgtcctgcac caggactggc tgaatggcaa ggagtacaag    2340
tgcaaggtct ccaacaaagc cctcccagcc cccatcgaga aaaccatctc caaagccaaa    2400
gggcagcccc gagaaccaca ggtgtacacc ctgcccccat cccgggatga gctgaccaag    2460
aaccaggtca gcctgacctg cctggtcaaa ggcttctatc ccagcgacat cgccgtggag    2520
tgggagagca atgggcagcc ggagaacaac tacaagacca cgcctcccgt gctggactcc    2580
gacggctcct tcttcctcta cagcaagctc accgtggaca gagcaggtg gcagcagggg    2640
aacgtcttct catgctccgt gatgcatgag gctctgcaca accactacac gcagaagagc    2700
ctctccctgt ctccgggtaa atagtctaga gctcgctgat cagcctcgac tgtgccttct    2760
agttgccagc catctgttgt ttgccccctc ccgtgccttt ccttgaccct ggaaggtgcc    2820
actcccactg tcctttccta ataaaatgag gaaattgcat cgcattgtct gagtaggtgt    2880
cattctattc tggggggtgg ggtggggcag gacagcaagg gggaggattg ggaagacaat    2940
```

```
agcaggcatg ctggggatgc ggtgggctct atggcttctg aggcggaaag aaccagctgg   3000
ggctcgagcg tgggccatcg ccctgataga cggttttcg ccctttgacg ttggagtcca    3060
cgttctttaa tagtggactc ttgttccaaa ctggaacaac actcaaccct atctcggtct   3120
attcttttga tttataaggg attttgccga tttcggccta ttggttaaaa aatgagctga   3180
tttaacaaat atttaacgcg aattttaaca aaatattaac gtttacaatt tcgcctgatg   3240
cggtattttc tccttacgca tctgtgcggt atttcacacc gcatacgcgg atctgcgcag   3300
caccatggcc tgaaataacc tctgaaagag gaacttggtt aggtaccttc tgaggcggaa   3360
agaaccagct gtggaatgtg tgtcagttag ggtgtggaaa gtccccaggc tccccagcag   3420
gcagaagtat gcaaagcatg catctcaatt agtcagcaac caggtgtgga agtccccag    3480
gctcccccagc aggcagaagt atgcaaagca tgcatctcaa ttagtcagca accatagtcc   3540
cgcccctaac tccgcccatc ccgcccctaa ctccgcccag ttccgcccat tctccgcccc   3600
atggctgact aatttttttt atttatgcag aggccgaggc cgcctcggcc tctgagctat   3660
tccagaagta gtgaggaggc ttttttggag gcctaggctt ttgcaaaaag cttgattctt   3720
ctgacacaac agtctcgaac ttaaggctag agccaccatg attgaacaag atggattgca   3780
cgcaggttct ccggccgctt gggtggagag gctattcggc tatgactggg cacaacagac   3840
aatcggctgc tctgatgccg ccgtgttccg gctgtcagcg caggggcgcc cggttctttt   3900
tgtcaagacc gacctgtccg gtgccctgaa tgaactgcag gacgaggcag cgcggctatc   3960
gtggctggcc acgacgggcg ttccttgcgc agctgtgctc gacgttgtca ctgaagcggg   4020
aagggactgg ctgctattgg gcgaagtgcc ggggcaggat ctcctgtcat ctcaccttgc   4080
tcctgccgag aaagtatcca tcatggctga tgcaatgcgg cggctgcata cgcttgatcc   4140
ggctacctgc ccattcgacc accaagcgaa acatcgcatc gagcgagcac gtactcggat   4200
ggaagccggt cttgtcgatc aggatgatct ggacgaagag catcaggggc tcgcgccagc   4260
cgaactgttc gccaggctca aggcgcgcat gcccgacggc gaggatctcg tcgtgaccca   4320
tggcgatgcc tgcttgccga atatcatggt ggaaaatggc cgcttttctg gattcatcga   4380
ctgtggccgg ctgggtgtgg cggaccgcta tcaggacata gcgttggcta cccgtgatat   4440
tgctgaagag cttggcggcg aatgggctga ccgcttcctc gtgctttacg gtatcgccgc   4500
tcccgattcg cagcgcatcg ccttctatcg ccttcttgac gagttcttct gagcgggact   4560
ctggggttcg aaatgaccga ccaagcgacg cccaacctgc catcacgatg gccgcaataa   4620
aatatcttta ttttcattac atctgtgtgt tggttttttg tgtgaatcga tagcgataag   4680
gatcgatcct ctagctagag tcgatcgacc tgcagggatc gcgtatggt gcactctcag   4740
tacaatctgc tctgatgccg catagttaag ccagccccga cacccgccaa cacccgctga   4800
cgcgccctga cgggcttgtc tgctcccggc atccgcttac agacaagctg tgaccgtctc   4860
cgggagctgc atgtgtcaga ggttttcacc gtcatcaccg aaacgcgcga cgcgaagggg   4920
cctcgtgata cgcctatttt tataggttaa tgtcatgata ataatggttt cttagacgtc   4980
aggtggcact tttcggggaa atgtgcgcgg aaccccctatt tgtttatttt tctaaataca   5040
ttcaaatatg tatccgctca tgagacaata accctgataa atgcttcaat aatattgaaa   5100
aaggaagagt atgagtattc aacatttccg tgtcgccctt attcccttt ttgcggcatt    5160
ttgccttcct gtttttgctc acccagaaac gctggtgaaa gtaaaagatg ctgaagatca   5220
gttgggtgca cgagtgggtt acatcgaact ggatctcaac agcggtaaga tccttgagag   5280
```

```
ttttcgcccc gaagaacgtt ttccaatgat gagcactttt aaagttctgc tatgtggcgc    5340
ggtattatcc cgtattgacg ccgggcaaga gcaactcggt cgccgcatac actattctca    5400
gaatgacttg gttgagtact caccagtcac agaaaagcat cttacggatg gcatgacagt    5460
aagagaatta tgcagtgctg ccataaccat gagtgataac actgcggcca acttacttct    5520
gacaacgatc ggaggaccga aggagctaac cgcttttttg cacaacatgg gggatcatgt    5580
aactcgcctt gatcgttggg aaccggagct gaatgaagcc ataccaaacg acgagcgtga    5640
caccacgatg cctgtagcaa tggcaacaac gttgcgcaaa ctattaactg gcgaactact    5700
tactctagct tcccggcaac aattaataga ctggatggag gcggataaag ttgcaggacc    5760
acttctgcgc tcggcccttc cggctggctg gtttattgct gataaatctg gagccggtga    5820
gcgtgggtct cgcggtatca ttgcagcact ggggccagat ggtaagccct cccgtatcgt    5880
agttatctac acgacgggga gtcaggcaac tatggatgaa cgaaatagac agatcgctga    5940
gataggtgcc tcactgatta agcattggta actgtcagac caagtttact catatatact    6000
ttagattgat ttaaaacttc attttttaatt taaaaggatc taggtgaaga tcctttttga    6060
taatctcatg accaaaatcc cttaacgtga gttttcgttc cactgagcgt cagaccccgt    6120
agaaaagatc aaaggatctt cttgagatcc ttttttttctg cgcgtaatct gctgcttgca    6180
aacaaaaaaa ccaccgctac cagcggtggt ttgtttgccg gatcaagagc taccaactct    6240
ttttccgaag gtaactggct tcagcagagc gcagatacca aatactgtcc ttctagtgta    6300
gccgtagtta ggccaccact tcaagaactc tgtagcaccg cctacatacc tcgctctgct    6360
aatcctgtta ccagtggctg ctgccagtgg cgataagtcg tgtcttaccg ggttggactc    6420
aagacgatag ttaccggata aggcgcagcg gtcgggctga acggggggtt cgtgcacaca    6480
gcccagcttg gagcgaacga cctacaccga actgagatac ctacagcgtg agctatgaga    6540
aagcgccacg cttcccgaag ggagaaaggc ggacaggtat ccggtaagcg cagggtcgg    6600 aacaggagag cgcacgaggg agcttccagg gggaaacgcc tggtatcttt atagtcctgt    6660
cgggtttcgc cacctctgac ttgagcgtcg attttttgtga tgctcgtcag ggggggcggag    6720 cctatggaaa aacgccagca acgcggcctt tttacggttc ctggccttttt gctggccttt    6780 tgctcacatg gctcgacaga tccgacggat cgggagatcc tagc                     6824
```

<210> SEQ ID NO 19
<211> LENGTH: 1344
<212> TYPE: DNA
<213> ORGANISM: Artificial Sequence
<220> FEATURE:
<223> OTHER INFORMATION: Synthetic Construct

<400> SEQUENCE: 19

```
caggcttatc tacagcagtc tggggctgag ctggtgaggc ctggggcctc agtgaagatg      60
tcctgcaagg cttctggcta cacatttacc agttacaata tgcactgggt aaagcagaca     120
cctagacagg gcctggaatg gattggaggt atttatccag gaaatggtga tacttcctac     180
aatcagaagt tcaagggcaa ggccacactg actgtaggca atcctccag cacagcctac     240 atgcagctca gcagcctgac atctgaagac tctgcggtct atttctgtgc aagatatgac     300
tacaactatg ctatggacta ctggggtcaa ggaacctcag tcaccgtctc ctcagcctcc     360
accaagggcc catcggtctt ccccctggca ccctcctcca agagcacctc tgggggcaca     420
gcggccctgg gctgcctggt caaggactac ttccccgaac cggtgacggt gtcgtggaac     480
tcaggcgccc tgaccagcgg cgtgcacacc ttcccggctg tcctacagtc ctcaggactc     540
```

```
tactccctca gcagcgtggt gaccgtgccc tccagcagct tgggcaccca gacctacatc    600
tgcaacgtga atcacaagcc cagcaacacc aaggtggaca gaaagttgag cccaaatct     660 tgtgacaaaa ctcacacatg cccaccgtgc ccagcacctg aactcctggg gggaccgtca    720
gtcttcctct tccccccaaa acccaaggac accctcatga tctcccggac ccctgaggtc    780
acatgcgtgg tggtggacgt gagccacgaa gaccctgagg tcaagttcaa ctggtacgtg    840
gacggcgtgg aggtgcataa tgccaagaca aagccgcggg aggagcagta caacagcacg    900
taccgtgtgg tcagcgtcct caccgtcctg caccaggact ggctgaatgg caaggagtac    960
aagtgcaagg tctccaacaa agccctccca gcccccatcg agaaaaccat ctccaaagcc   1020
aaagggcagc cccgagaacc acaggtgtac accctgcccc catcccggga tgagctgacc   1080
aagaaccagg tcagcctgac ctgcctggtc aaaggcttct atcccagcga catcgccgtg   1140
gagtgggaga gcaatgggca gccggagaac aactacaaga ccacgcctcc cgtgctggac   1200
tccgacggct ccttcttcct ctacagcaag ctcaccgtgg acaagagcag gtggcagcag   1260
gggaacgtct tctcatgctc cgtgatgcat gaggctctgc acaaccacta cacgcagaag   1320
agcctctccc tgtctccggg taaa                                          1344
```

<210> SEQ ID NO 20  
<211> LENGTH: 448  
<212> TYPE: PRT  
<213> ORGANISM: Artificial Sequence  
<220> FEATURE:  
<223> OTHER INFORMATION: Synthetic Construct

<400> SEQUENCE: 20

```
Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Arg Gln Gly Leu Glu Trp Ile
        35                  40                  45

Gly Gly Ile Tyr Pro Gly Asn Gly Asp Thr Ser Tyr Asn Gln Lys Phe
    50                  55                  60

Lys Gly Lys Ala Thr Leu Thr Val Gly Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Tyr Asp Tyr Asn Tyr Ala Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
```

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
        260                 265                 270

Glu Val Lys Phe Asn Trp Tyr Val Asp Gly Val Glu Val His Asn Ala
    275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
        340                 345                 350

Pro Pro Ser Arg Asp Glu Leu Thr Lys Asn Gln Val Ser Leu Thr Cys
    355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly Lys
    435                 440                 445

<210> SEQ ID NO 21
<211> LENGTH: 318
<212> TYPE: DNA
<213> ORGANISM: Homo sapiens

<400> SEQUENCE: 21
actgtggctg caccaagtgt cttcatcttc ccgccatctg atgagcagtt gaaatctgga        60
actgcctctg ttgtgtgcct gctgaataac ttctatccca gagaggccaa agtacagtgg       120
aaggtggata acgccctcca atcgggtaac tcccaggaga gtgtcacaga gcaggacagc       180
aaggacagca cctacagcct cagcagcacc ctgacgctga gcaaagcaga ctacgagaaa       240
cacaaagtct acgcctgcga agtcacccat caggcctga gctcgcccgt cacaaagagc       300
ttcaacaggg gagagtgt                                                    318

<210> SEQ ID NO 22
<211> LENGTH: 106
<212> TYPE: PRT
<213> ORGANISM: Homo sapiens

<400> SEQUENCE: 22

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser

```
                35                  40                  45
Gly Asn Ser Gln Glu Ser Val Thr Glu Gln Asp Ser Lys Asp Ser Thr
         50                  55                  60

Tyr Ser Leu Ser Ser Thr Leu Thr Leu Ser Lys Ala Asp Tyr Glu Lys
 65                  70                  75                  80

His Lys Val Tyr Ala Cys Glu Val Thr His Gln Gly Leu Ser Ser Pro
                 85                  90                  95

Val Thr Lys Ser Phe Asn Arg Gly Glu Cys
            100                 105
```

<210> SEQ ID NO 23
<211> LENGTH: 990
<212> TYPE: DNA
<213> ORGANISM: Homo sapiens

<400> SEQUENCE: 23

```
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agttgagccc     300
aaatcttgtg acaaaactca cacatgccca ccgtgcccag cacctgaact cctgggggga     360
ccgtcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcgggagga gcagtacaac     540
agcacgtacc gtgtggtcag cgtcctcacc gtcctgcacc aggactggct gaatggcaag     600
gagtacaagt gcaaggtctc caacaaagcc ctcccagccc ccatcgagaa aaccatctcc     660
aaagccaaag ggcagccccg agaaccacag gtgtacaccc tgcccccatc ccgggatgag     720
ctgaccaaga accaggtcag cctgacctgc ctggtcaaag gcttctatcc cagcgacatc     780
gccgtggagt gggagagcaa tgggcagccg gagaacaact acaagaccac gcctcccgtg     840
ctggactccg acggctcctt cttcctctac agcaagctca ccgtggacaa gagcaggtgg     900
cagcagggga acgtcttctc atgctccgtg atgcatgagg ctctgcacaa ccactacacg     960
cagaagagcc tctccctgtc tccgggtaaa                                     990
```

<210> SEQ ID NO 24
<211> LENGTH: 330
<212> TYPE: PRT
<213> ORGANISM: Homo sapiens

<400> SEQUENCE: 24

```
Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80
```

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 25
<211> LENGTH: 321
<212> TYPE: DNA
<213> ORGANISM: Mus musculus

<400> SEQUENCE: 25
caaattgttc tctcccagtc tccagcaatc ctgtctgcat ctccagggga gaaggtcaca      60
atgacttgca gggccagctc aagtgtaagt tacatgcact ggtaccagca gaagccagga     120
tcctccccca aaccctggat ttatgccaca tccaacctgg cttctggagt ccctgctcgc     180
ttcagtggca gtgggtctgg gacctcttat tctttcacaa tcagcagagt ggaggctgaa     240
gatgctgcca cttattactg ccagcagtgg acttttaacc cacccacgtt cggaggggg     300 accaggctgg aaataaaacg g                                              321

<210> SEQ ID NO 26
<211> LENGTH: 107
<212> TYPE: PRT
<213> ORGANISM: Mus musculus

<400> SEQUENCE: 26

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Phe Thr Ile Ser Arg Val Glu Ala Glu
65                  70                  75                  80

Asp Ala Ala Thr Tyr Tyr Cys Gln Gln Trp Thr Phe Asn Pro Pro Thr
                85                  90                  95

Phe Gly Gly Gly Thr Arg Leu Glu Ile Lys Arg
            100                 105

<210> SEQ ID NO 27
<211> LENGTH: 645
<212> TYPE: DNA
<213> ORGANISM: Artificial Sequence
<220> FEATURE:
<223> OTHER INFORMATION: Synthetic Construct

<400> SEQUENCE: 27
caaattgttc tctcccagtc tccagcaatc ctgtctgcat ctccagggga gaaggtcaca      60
atgacttgca gggccagctc aagtgtaagt tacatgcact ggtaccagca gaagccagga    120
tcctccccca aaccctggat ttatgccaca tccaacctgg cttctggagt ccctgctcgc    180
ttcagtggca gtgggtctgg gacctcttat tctttcacaa tcagcagagt ggaggctgaa    240
gatgctgcca cttattactg ccagcagtgg acttttaacc cacccacgtt cggagggggg    300
accaggctgg aaataaaacg gactgtggct gcaccaagtg tcttcatctt cccgccatct    360
gatgagcagt tgaaatctgg aactgcctct gttgtgtgcc tgctgaataa cttctatccc    420
agagaggcca agtacagtg gaaggtggat aacgccctcc aatcgggtaa ctcccaggag    480
agtgtcacag agcaggacag caaggacagc acctacagcc tcagcagcac cctgacgctg    540
agcaaagcag actacgagaa acacaaagtc tacgcctgcg aagtcaccca tcagggcctg    600
agctcgcccg tcacaaagag cttcaacagg ggagagtgtt agtga                    645

<210> SEQ ID NO 28
<211> LENGTH: 213
<212> TYPE: PRT
<213> ORGANISM: Artificial Sequence
<220> FEATURE:
<223> OTHER INFORMATION: Synthetic Construct

<400> SEQUENCE: 28

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Phe Thr Ile Ser Arg Val Glu Ala Glu
65                  70                  75                  80

Asp Ala Ala Thr Tyr Tyr Cys Gln Gln Trp Thr Phe Asn Pro Pro Thr
                85                  90                  95

Phe Gly Gly Gly Thr Arg Leu Glu Ile Lys Arg Thr Val Ala Ala Pro

```
                    100                 105                 110
Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 29
<211> LENGTH: 46
<212> TYPE: DNA
<213> ORGANISM: Artificial Sequence
<220> FEATURE:
<223> OTHER INFORMATION: Primer

<400> SEQUENCE: 29
tgaagacact tggtgcagcc acagtccgtt ttatttccag cctggt            46
```

ANTIBODY METHOD FOR TREATMENT OF A DISEASE IN WHICH THE TARGET CELLS ARE CELLS WHICH EXPRESS CD20

This application is a continuation of application Ser. No. 11/793,138, filed on Aug. 14, 2008, now U.S. Pat. No. 9,234,045 issued on Jan. 12, 2016, which was filed as PCT International Application No. PCT/FR2005/003123 on Dec. 14, 2005, which claims the benefit under 35 U.S.C. § 119(a) to Patent Application No. 0413320, filed in FRANCE on Dec. 15, 2004, all of which are hereby expressly incorporated by reference into the present application.

REFERENCE TO SEQUENCE LISTING SUBMITTED VIA EFS-WEB

This application includes an electronically submitted sequence listing in .txt format. The .txt file contains a sequence listing entitled "20151014_3493_0456PUS2_ST25.txt" created on Oct. 14, 2015 and is 56,116 bytes in size. The sequence listing contained in this .txt file is part of the specification and is hereby incorporated by reference herein in its entirety.

The present invention relates to a monoclonal antibody directed against the CD20 antigen, in which the variable regions of each of the light chains are encoded by sequences which share at least 70% sequence identity with murine nucleic acid sequence SEQ ID No. 5, the variable region of each of the heavy chains are encoded by sequences which share at least 70% identity with murine nucleic acid sequence SEQ ID No. 7, and the constant regions of the light and heavy chains are constant regions from a non-murine species, as well as to the use of such an antibody for activating FcγRIII receptors in immune effector cells and for the manufacture of a drug, in particular for the treatment of leukaemia or lymphoma.

INTRODUCTION AND PRIOR ART

The CD20 antigen is a hydrophobic transmembrane protein with a molecular weight of 35-37 kDa which is present on the surface of mature B lymphocytes (Valentine et al. (1987) *Proc. Natl. Acad. Sci. USA* 84(22): 8085-8089; Valentine et al. (1989) *J. Biol. Chem.*, 264(19): 11282-11287). It is expressed during the development of B lymphocyte cells (B cells) as from the early pre-B stage until differentiation into plasmocytes, a stage at which this expression disappears. The CD20 antigen is present on both normal B lymphocytes and malign B cells. More specifically, the CD20 antigen is expressed on most phenotype-B lymphomas (80% lymphomas): for example, it is expressed on over 90% non-Hodgkin's B-cell lymphomas (NHL) and over 95% B-type Chronic Lymphocytic Leukaemia (B-CLL). The CD20 antigen is not expressed on haematopoietic stem cells and on plasmocytes.

The function of CD20 has not yet been fully clarified, but it may act as a calcium channel and be involved in the regulation of the first stages of B lymphocytes differentiation (Golay et al. (1985) *J. Immunol.* 135(6): 3795-3801) and proliferation (Tedder et al. (August 1986) *Eur. J. Immunol.* 16(8): 881-887).

Therefore, although some uncertainty remains as regards its role in the activation and proliferation of B cells, the CD20 antigen is, because of its location, an important target for the treatment of conditions which involve tumoural B cells, such as NHL or B-CLL for instance, using antibodies which specifically recognise CD20. Furthermore, this antigen is an ideal target since it is a membrane protein for which no expression modulation or polymorphism is known.

Only one non-radioactively labelled anti-CD20 monoclonal antibody, Rituxan® (rituximab, Genentech), is currently commercially available for the treatment of B-cell lymphoma. It shows encouraging clinical results in patients with NHL when associated with chemotherapy. Its effectiveness, however, remains variable and frequently modest when it is used alone (Teeling et al. (2004) *Blood* 104(6): 1793-1800).

In addition, Rituxan® has only a modest effect on B cells in B-CLL. This low degree of effectiveness has been correlated with various phenomena: on the one hand, B-CLL B cells only express CD20 in relatively low quantities, and on the other hand, Rituxan® only induces very low ADCC (Antibody-Dependent Cellular Cytotoxicity) activity levels against these cells in vitro. These two observations might explain the correlation that has been observed between the level of expression of CD20 on tumours (in quantitative flow cytometry) and response to treatments.

Since B-CLL is the commonest form of leukaemia in western countries, and high-dose chemotherapy treatment sometimes prove to be insufficient and involve side effects which lead to haematopoietic aplasia and immunodeficiency, monoclonal antibodies appear to be an innovative approach. It is therefore of primary importance to develop antibodies which are capable of specifically targeting the CD20 antigen and which allow tumour cells such as B-CLL, which only express this antigen to a limited degree, to be destroyed.

Antibodies 2F2 and 7D8, proposed by Genmab (Teeling et al. (2004) *Blood* 104(6): 1793-1800) for the treatment of B-CLL, have a capacity to activate the complement which is greater than that induced by Rituxan®. These antibodies, however, have a low ADCC activity, similar to that of Rituxan®. Yet, some clinicians have shown that the complement activity is the cause of deleterious side effects, as the antibodies trigger an activation system which leads to the production of molecules (in particular, anaphylatoxins) which have a wide spectrum of non-specific activities (inflammatory, allergic or vascular reactions etc.). In addition, these antibodies are still at the research stage and their clinical effectiveness has yet to be evaluated.

In application FR03/02713 (WO 2004/029092), the present Applicant describes an anti-CD20 antibody which can be produced in the YB2/0 line and which has been selected for its ability to induce a high ADCC activity and a high level of IL-2 production by the Jurkat-CD16 cell compared to Rituxan®. There is a significant need for new anti-CD20 antibodies which will allow the range of B-cell diseases treated using the currently available immunotherapies to be extended; this is particularly the case with B-cell diseases in which the CD20 antigen is expressed to a small degree on the populations of B cells involved, and for which no satisfactory immunotherapies exist.

It is with this purpose in mind that the present Applicant has developed new CD20 antibodies which exhibit a particularly high ADCC activity compared to Rituxan®.

DESCRIPTION

A first object of the invention therefore relates to a monoclonal antibody directed against the CD20 antigen, in which the variable region of each of the light chains is encoded by a sequence which shares at least 70% identity with murine nucleic acid sequence SEQ ID No. 5, the variable region of each of the heavy chains is encoded by a sequence which shares at least 70% identity with murine nucleic acid sequence SEQ ID No. 7, and the constant regions of the light and heavy chains are constant regions from a non-murine species.

The antibodies are made up of heavy and light chains linked together by disulphide bonds. Each chain is made up, in the N-terminal position, of a variable region (or domain) (encoded by rearranged V-J genes for the light chains and V-D-J genes for the heavy chains) specific to the antigen against which the antibody is directed, and, in the C-terminal position, of a constant region made up from a single CL domain for the light chains, or several domains for the heavy chains.

For the purposes of the invention, the expressions "monoclonal antibodies" or "monoclonal antibody composition" refer to a preparation of antibody molecules having identical and unique specificities.

The antibody according to the invention, in which the variable regions in the light and heavy chains are from a species which is different from that of the constant regions of the light and heavy chains, is referred to as a "chimeric" antibody.

Murine nucleic acid sequences SEQ ID No. 5 and SEQ ID No. 7 code for the variable domain of each of the light chains and the variable domain of each of the heavy chains respectively, of the antibody produced by murine hybridoma CAT-13.6E12, available at the Deutsche Sammlung von Mikroorganismen and Zellkulturen GmbH (DSMZ) under number ACC 474. This hybridoma produces a murine IgG2a, κ-type monoclonal antibody directed against CD20.

These murine sequences were chosen to derive the sequences of the variable regions of the antibodies according to the invention because of the specificity of the CAT-13.6E12 murine antibody for the CD20 antigen, the antigen also recognised by Rituxan®. The variable regions of the antibodies according to the invention share at least 70% identity with sequences SEQ ID No. 5 and SEQ ID No. 7, with this sequence identity providing the antibodies according to the invention with a specificity which is identical to that of the CAT-13.6E2 murine antibody. Preferably, this sequence identity also provides the antibody according to the invention with an affinity for the target which is identical to that of the CAT-13.6E12 murine antibody.

In addition, the present Applicant has surprisingly shown that the CAT-13.6E12 murine antibody has the ability to induce the secretion of IL-2 in the presence of Jurkat-CD16 cells which express ectodomains of the FcγRIIIA receptor (as shown in FIG. 11), indicating a strong binding between the murine antibody and human CD16 (FcγRIIIA), which again motivated the choice made by the present Applicant.

In addition, in the antibodies according to the invention, the constant regions of the light and heavy chains are from a non-murine species. In this regard all non-murine mammal species and families may be used, in particular humans, monkeys, murine (apart from mice), porcine, bovine, equine, feline, canine, as well as birds.

The antibodies according to the invention may be constructed using standard recombinant DNA techniques, well known to those skilled in the art, and more particularly using the "chimeric" antibody construction techniques described, for example, in Morrison et al. (1984) *Proc. Natl. Acad. Sci. USA* 81: 6851-6855, where the recombinant DNA technology is used to replace the constant region of a heavy chain and/or the constant region of a light chain in an antibody from a non-human mammal, with the corresponding regions in an human immunoglobulin. One particular embodiment will be illustrated below.

Advantageously, the variable region of each of the light chains of the antibody according to the invention is encoded by a sequence which shares at least 80% identity with murine nucleic acid sequence SEQ ID No. 5, and the variable region of each of the heavy chains of the antibody according to the invention is encoded by a sequence which shares at least 80% identity with murine nucleic acid sequence SEQ ID No. 7.

Advantageously, the variable region of each of the light chains of the antibody according to the invention is encoded by a sequence which shares at least 90% identity with murine nucleic acid sequence SEQ ID No. 5, and the variable region of each of the heavy chains of the antibody according to the invention is encoded by a sequence which shares at least 90% identity with murine nucleic acid sequence SEQ ID No. 7.

Advantageously, the variable region of each of the light chains of the antibody according to the invention is encoded by a sequence which shares at least 95% identity with murine nucleic acid sequence SEQ ID No. 5, and the variable region of each of the heavy chains of the antibody according to the invention is encoded by a sequence which shares at least 95% identity with murine nucleic acid sequence SEQ ID No. 7.

Advantageously, the variable region of each of the light chains of the antibody according to the invention is encoded by a sequence which shares at least 99% identity with murine nucleic acid sequence SEQ ID No. 5, and the variable region of each of the heavy chains of the antibody according to the invention is encoded by a sequence which shares at least 99% identity with murine nucleic acid sequence SEQ ID No. 7.

Advantageously, the invention also relates to any antibody in which the variable regions of the heavy and light chains include one or more substitution(s), insertion(s) or deletion(s) of one or more amino acids, with these sequence modifications complying with the sequence identity percentage levels defined above, without affecting the antibodys' specificity or affinity for the target.

The antibodies of the invention are also any antibody which includes the CDRs (Complementary Determining Regions) of the CAT-13.6E12 antibody, combined with FR (framework) regions (highly conserved regions of the variable regions, also known as "backbone" regions). Such antibodies have affinities and specificities which are closely comparable with, and preferably identical to, those of the CAT-13.6E12 murine antibody.

Preferably, the variable region of each of the light chains of the antibody according to the invention is encoded by murine nucleic acid sequence SEQ ID No. 5 or by murine nucleic acid sequence SEQ ID No. 25, and the variable region of each of the heavy chains of the antibody according to the invention is encoded by murine nucleic acid sequence SEQ ID No. 7.

In one embodiment of the invention, an antibody according to the invention is therefore a monoclonal antibody directed against the CD20 antigen, in which the variable region of each of the light chains is encoded by murine nucleic acid sequence SEQ ID No. 5, the variable region of each of the heavy chains is encoded by murine nucleic acid sequence SEQ ID No. 7, and the constant regions of the light and heavy chains are constant regions from a non-murine species.

In a second embodiment, the antibody according to the invention is therefore a monoclonal antibody raised against the CD20 antigen, in which the variable regions of each of the light chains are encoded by murine nucleic acid sequence SEQ ID No. 25, the variable regions of each of the heavy chains are encoded by murine nucleic acid sequence SEQ ID No. 7, and the constant regions of the light and heavy chains are constant regions from a non-murine species.

In both embodiments, the antibodies differ in their nucleotide sequences by a single nucleotide: the nucleotide located at position 318 in SEQ ID No. 5 and SEQ ID No. 25, which correspond to a cytosine and an adenine respectively.

The antibodies of the invention according to these embodiments have specificities and affinities for the target antigen, CD20, which are comparable with, and preferably identical to, those of the CAT-13.6E12 murine antibody.

Preferably, the constant regions of each of the light chains and each of the heavy chains of the antibody according to the invention are human constant regions. In this preferred embodiment of the invention, the immunogenicity of the antibody is reduced in humans, and consequently, the antibodys' effectiveness is improved upon therapeutic administration to humans.

According to a preferred embodiment of the invention, the constant region of each of the light chains of the antibody according to the invention is of κ type. Any allotype is suitable for the implementation of the invention, e.g. Km(1), Km(1, 2), Km(1, 2, 3) or Km(3), but the preferred allotype is Km(3).

According to another additional embodiment, the constant region of each of the light chains of the antibody according to the invention is of λ type.

According to one specific aspect of the invention, and in particular when the constant regions of each of the light chains and of each of the heavy chains of the antibody according to the invention are human regions, the constant region of each of the heavy chains of the antibody is of γ type. According to this alternative, the constant region of each of the heavy chains of the antibody may be of γ1, γ2 or γ3 type, with these three constant region types exhibiting the specific feature of binding the human complement, or even of γ4 type. Antibodies which have γ-type constant regions for each of the heavy chains belong to the IgG class. Immunoglobulins G (IgG) are heterodimers made up of 2 heavy chains and 2 light chains, linked together by disulphide bonds. Each chain is made up, in the N-terminal position, of a variable region or domain (encoded by rearranged V-J genes for the light chains and V-D-J genes for the heavy chains) specific to the antigen against which the antibody is directed, and, in the C-terminal position, of a constant region made up of a single CL domain for the light chain, or of 3 domains ($CH_1$, $CH_2$ and $CH_3$) for the heavy chain. Combining the variable domains and the $CH_1$ and CL domains of the heavy and light chains make up the Fab fragments which are linked to the Fc regions through a highly flexible hinge region allowing each Fab fragment to bind its antigen target whilst the Fc region, the mediator for the effector properties of the antibody, remains accessible to effector molecules such as FcγR and C1q receptors. The Fc region, made up of both $CH_2$ and $CH_3$ globular domains, is glycosylated at the $CH_2$ domain, with a lactosamine-type biantennary N-glycan linked to Asn 297 being present on each of the 2 chains.

Preferably, the constant region of each of the heavy chains of the antibody is of γ1 type, as such antibody exhibits the ability to induce ADCC activity in the greatest number of (human) individuals. In this respect, any allotype is suitable for the implementation of the invention, e.g. G1m(3), G1m(1, 2, 17), G1m(1, 17) or G1m(1, 3). Preferably, the allotype is G1m(1, 17).

According to one particular aspect of the invention, the constant region of each of the heavy chains of the antibody is of γ1 type, and is encoded by human nucleic acid sequence SEQ ID No. 23, with the constant region of each of the light chains being encoded by human nucleic acid sequence SEQ ID No. 21. Such an antibody therefore includes a murine variable region and a human constant region, with γ1-type heavy chains. This antibody therefore belongs to the IgG1 sub-class. According to the embodiment of the antibody according to the invention, the antibody has two light chains, the variable domain of which is encoded by murine nucleic acid sequence SEQ ID No. 5 or murine nucleic acid sequence SEQ ID No. 25, and the human constant region of which is encoded by nucleic acid sequence SEQ ID No. 21, and two heavy chains, the variable domain of which is encoded by murine nucleic acid sequence SEQ ID No. 7 and the constant region of which is encoded by human nucleic acid sequence SEQ ID No. 23.

Preferentially, each of the light chains of the antibody according to the invention is encoded by murine-human chimeric nucleic acid sequence SEQ ID No. 13 or by murine-human chimeric nucleic acid sequence SEQ ID No. 27, and each of the heavy chains is encoded by murine-human chimeric nucleic acid sequence SEQ ID No. 19. Murine-human chimeric nucleic acid sequence SEQ ID No. 13, which codes for each of the light chains of the antibody, is obtained by fusing murine nucleic acid sequence SEQ ID No. 5, which codes for the variable domain of each of the light chains of the antibody, to human nucleic acid sequence SEQ ID No. 21, which codes for the constant region of each of the light chains of the antibody.

Murine-human chimeric nucleic acid sequence SEQ ID No. 27, which codes for each of the light chains of the antibody, is obtained by fusing murine nucleic acid sequence SEQ ID No. 25, which codes for the variable domain of each of the light chains of the antibody, to human nucleic acid sequence SEQ ID No. 21, which codes for the constant region of the light chains of the antibody.

Murine-human chimeric nucleic acid sequence SEQ ID No. 19, which codes for each of the heavy chains of the antibody, is obtained by fusing murine nucleic acid sequence SEQ ID No. 7, which codes for the variable domain of each of the heavy chains of the antibody, to human nucleic acid sequence SEQ ID No. 23, which codes for the constant region of each of the heavy chains of the antibody.

According to a particular aspect of the invention, when each of the light chains of the antibody is encoded by murine-human chimeric nucleic acid sequence SEQ ID No. 13, and each of the heavy chains is encoded by murine-human chimeric nucleic acid sequence SEQ ID No. 19, the peptide sequence of each of the light chains, deduced from nucleic acid sequence SEQ ID No. 13, is sequence SEQ ID No. 14 and the peptide sequence of each of the heavy chains, deduced from nucleic acid sequence SEQ ID No. 19, is sequence SEQ ID No. 20.

According to a further particular aspect of the invention, when each of the light chains of the antibody is encoded by murine-human chimeric nucleic acid sequence SEQ ID No. 27, and each of the heavy chains is encoded by murine-human chimeric nucleic acid sequence SEQ ID No. 19, the peptide sequence of each of the light chains, deduced from nucleic acid sequence SEQ ID No. 27, is sequence SEQ ID No. 28, and the peptide sequence of each of the heavy chains, deduced from nucleic acid sequence SEQ ID No. 19, is sequence SEQ ID No. 20.

The peptide sequences SEQ ID No. 14 and SEQ ID No. 28 differ only by the amino acid present at position 106 on each of these two sequences. The amino acid located at position 106 is lysine (K) in sequence SEQ ID No. 28; it is asparagine (N) in sequence SEQ ID No. 14.

The invention also relates to antibodies in which each of the light chains encoded by murine-human chimeric nucleic acid sequence shares at least 70% homology or identity with murine-human chimeric nucleic acid sequence SEQ ID No. 13, and each of the heavy chains encoded by a murine-human chimeric nucleic acid sequence shares at least 70% homology or identity with the murine-human chimeric nucleic acid sequence SEQ ID No. 19, with these modifications adversely impairing neither the specificity of the antibody nor its effector activities, such as ADCC (Antibody-Dependent Cell-mediated Cytotoxicity) activity.

In a particularly advantageous manner, the antibody of the invention is produced by a rat hybridoma cell line. The line which produces the antibody according to the invention is an important characteristic since it provides the antibody with certain of its particular properties. In fact, the method of expression of the antibody induces the post-translational modifications, in particular the glycosylation modifications, which may vary from one cell line to another, and therefore provides antibodies which have identical primary structures with different functional properties.

In a preferred embodiment, the antibody is produced in the rat hybridoma YB2/0 cell line (cell YB2/3HL.P2.G11.16Ag.20, registered at the American Type Culture Collection under ATCC number CRL-1662). This line was chosen because of its ability to produce antibodies with improved ADCC activity compared to antibodies with the same primary structures produced, for example, in CHO cells.

According to a specific embodiment, a preferred antibody according to the invention is antibody EMAB6 produced by clone R509, registered on 8 Nov. 2004 under registration number CNCM I-3314 at the Collection Nationale de Cultures de Microorganismes (CNCM, Institut Pasteur, 25 rue du Docteur Roux, 75724 Paris Cedex 15, France). Each of the light chains of the EMAB6 antibody is encoded by murine-human chimeric nucleic acid sequence SEQ ID No. 13, and each of the heavy chains is encoded by murine-human chimeric nucleic acid SEQ ID No. 19. This chimeric antibody competes with the CAT-13.6E12 murine antibody in binding CD20 and has a cytotoxic activity which is much greater than that of Rituxan®, which may be attributable in part to the specific glycosylation of the N-glycan of the heavy chain of these antibodies (see Example 4). In fact, a specific feature of the R509 clone is that it produces an EMAB6 antibody composition with a fucose/galactose ratio of less than 0.6, which has been shown, in patent application FR 03 12229, to be optimal to provide the antibody with strong ADCC activity. This antibody is therefore particularly interesting as a therapeutic tool for the treatment of conditions in which the cells to be targeted express CD20.

In a further specific embodiment, another preferred antibody according to the invention is antibody EMAB603 produced by clone R603, registered on 29 Nov. 2005 under registration number CNCM I-3529 at the Collection Nationale de Cultures de Microorganismes (CNCM, Institut Pasteur, 25 rue du Docteur Roux, 75724 Paris Cedex 15, France). Each of the light chains of the EMAB603 antibody is encoded by murine-human chimeric nucleic acid sequence SEQ ID No. 27, and each of the heavy chains is encoded by murine-human chimeric amino acid sequence SEQ ID No. 19. This chimeric antibody competes with the CAT-13.6E12 murine antibody in binding CD20 and has a cytotoxic activity which is much greater than that of Rituxan®, which may be attributable in part to the specific glycosylation of the N-glycan of the heavy chain of these antibodies (see Example 3). In fact, a specific feature of the R603 clone is that it produces an EMAB603 antibody composition with a fucose/galactose ratio of less than 0.6, (see Example 4) which has been shown, in patent application FR 03 12229, to be optimal to provide the antibody with strong ADCC activity. This antibody is therefore of particular interest as a therapeutic tool for the treatment of conditions in which the cells to be targeted express CD20.

Another object of the invention relates to vector pEF-EMAB6-K for the expression of the light chain of an antibody according to the invention, having sequence SEQ ID No. 12. This vector is the vector which allows an antibody according to the invention, the light chain of which is encoded by nucleic acid sequence SEQ ID No. 13, the deduced peptide sequence of which is sequence SEQ ID No. 14, to be expressed. This vector is a nucleic acid molecule into which murine nucleic acid sequence SEQ ID No. 5, which codes for the variable domain of each of the light chains of the antibody, and nucleic acid sequence SEQ ID No. 21, which codes for the constant regions of each of the light chains of the antibody, have been inserted to be introduced and maintained in a host cell. It allows foreign nucleic acid fragments to be expressed in the host cell since it has sequences (promoter, polyadenylation sequence, selection gene) which are essential to this expression. Such vectors are well known to those skilled in the art and may be, without implied limitation, an adenovirus, a retrovirus, a plasmid or a bacteriophage. In addition, any mammalian cell may be used as a host cell, that is as a cell which expresses the antibody according to the invention, e.g. YB2/0, CHO, CHO dhfr- (e.g. CHO DX B11, CHO DG44), CHO Lec13, SP2/0, NS0, 293, BHK or COS.

Another object of the invention relates to vector pEF-EMAB6-H for the expression of the heavy chain of an antibody according to the invention, having sequence SEQ ID No. 18. This vector is the vector which allows an antibody according to the invention, the heavy chain of which is encoded by nucleic acid sequence SEQ ID NO 19, the deduced peptide sequence of which is sequence SEQ ID No. 20, to be expressed. This vector is a nucleic acid molecule into which murine nucleic acid sequence SEQ ID No. 7, which codes for the variable domain of each of the heavy chains of the antibody, and human nucleic acid sequence SEQ ID No. 23, which codes for the constant region of each of the heavy chains of the antibody, have been inserted to be introduced and maintained in a host cell. It allows these foreign nucleic acid fragments to be expressed in the host cell since it has sequences (promoter, polyadenylation sequence, selection gene) which are essential to this expression. Just as indicated earlier, the vector may be, for example, a plasmid, an adenovirus, a retrovirus or a bacteriophage, and the host cell may be any mammalian cell, e.g. YB2/0, CHO, CHO dhfr- (CHO DX B11, CHO DG44), CHO Lec13, SP2/0, NS0, 293, BHK or COS.

An antibody produced by co-expressing the pEF-EMAB6-K and pEF-EMAB6-H vectors in the YB2/0 cell is illustrated by the anti-CD20 EMAB6 antibody, produced by clone R509 (registered under registration number CNCM I-3314 at the CNCM). This antibody induces a cytotoxicity which is greater than that induced by Rituxan®, both in cells from patients with B-CLL (on which the CD20 antigen is expressed at lower levels) and in Raji cells used as a model and which express CD20 at higher densities compared to the cells from patients with B-CLL. Furthermore, the EMAB6 antibody induces a secretion of IL-2 (interleukin 2) in Jurkat-CD16 cells which is at much higher levels than with Rituxan®. Since the EMAB6 antibody can be produced by growing the R509 clone in a culture medium and under conditions which allow the vectors described above to be expressed, it is therefore a very interesting tool for advancing the therapy and diagnosis of B-cell diseases in which the CD20 antigen is involved, more specifically B-CLL, as well as for research in this area.

A particular object of the invention is a stable cell line which expresses an antibody according to the invention.

Advantageously, the stable cell line which expresses an antibody according to the invention is selected from the group consisting of: SP2/0, YB2/0, IR983F, a human myeloma such as Namalwa or any other cell of human origin such as PERC6, the CHO lines, in particular CHO-K-1, CHO-Lec10, CHO-Lec1, CHO-Lec13, CHO Pro-5, CHO dhfr- (CHO DX B11, CHO DG44), or other lines chosen from Wil-2, Jurkat, Vero, Molt-4, COS-7, 293-HEK, BHK, K$^6$H$^6$, NSO, SP2/0-Ag 14 and P3X63Ag8.653.

The line used is preferably the rat hybridoma YB2/0 cell line. This line was chosen because of its ability to produce antibodies with improved ADCC activity with respect to antibodies with the same primary structure produced, for example, in CHO cells.

According to one particular aspect of the invention, the stable cell line which expresses an antibody according to the invention and which is more specifically chosen from the group described above, has incorporated the two pEF-EMAB6-K and pEF-EMAB6-H expression vectors as described earlier.

One specific aspect of the invention relates to clone R509, registered under registration number CNCM I-3314 at the Collection Nationale de Cultures de Microorganismes (CNCM).

One specific aspect of the invention relates to clone R603, registered under registration number CNCM I-3529 at the Collection Nationale de Cultures de Microorganismes (CNCM).

Another object of the invention relates to a DNA fragment having sequence SEQ ID No. 19 which codes for the heavy chain of an antibody according to the invention. Murine-human chimeric nucleic acid sequence SEQ ID No. 19 codes for each of the heavy chains of the antibody. It is obtained by fusing murine nucleic acid sequence SEQ ID No. 7, which codes for the variable domain of each of the heavy chains of the antibody, to human nucleic acid sequence SEQ ID No. 23, which codes for the constant region of each of the heavy chains of the antibody.

Another specific object of the invention relates to a DNA fragment having sequence SEQ ID No. 13, which codes for the light chain of an antibody according to the invention. Murine-human chimeric nucleic acid sequence SEQ ID No. 13 codes for each of the light chains of the antibody. It is obtained by fusing murine nucleic acid sequence SEQ ID No. 5, which codes for the variable domain of each of the light chains of the antibody, to human nucleic acid sequence SEQ ID No. 21, which codes for the constant region of each of the light chains of the antibody.

Another specific object of the invention relates to a DNA fragment having sequence SEQ ID No. 27, which codes for the light chain of an antibody according to the invention. Murine-human chimeric nucleic acid sequence SEQ ID No. 27, codes for each of the light chains of the antibody. It is obtained by fusing murine nucleic acid sequence SEQ ID No. 25, which codes for the variable domain of each of the light chains of the antibody, to human nucleic acid sequence SEQ ID No. 21, which codes for the constant region of each of the light chains of the antibody.

One specific object of the invention relates to the use of the antibody according to the invention to activate, in vivo or in vitro, the FcγRIIIA receptors of effector immune cells. In fact, the antibodies of the invention have the specific feature and advantage of being cytotoxic. As such, they exhibit the ability to activate FcγRIIIA receptor with their Fc regions. This is of considerable interest as this receptor is expressed on the surface of cells known as "effector cells": binding of the Fc region of the antibody to its receptor carried by the effector cell causes the activation of FcγRIIIA receptors and the destruction of the target cells. Effector cells are, for instance, NK (Natural Killer) cells, macrophages, neutrophils, CD8 lymphocytes, Tγδ lymphocytes, NKT cells, eosinophils, basophils or mastocytes.

In one specific aspect, the antibody of the invention is used as a drug. Advantageously, such a drug is intended for the treatment of conditions in which the target cells are cells which express CD20, such as malignant B-cell lymphoma.

According to one advantageous aspect, the antibody according to the invention is used to manufacture a drug for the treatment of leukaemia or lymphoma.

One specific object of the invention is the use of the antibody according to the invention for the manufacture of a drug for the treatment of a pathology selected from the group consisting of acute B lymphoblastic leukaemia, B-cell lymphoma, mature B-cell lymphoma, including B-type Chronic Lymphocytic Leukaemia (B-CLL), small B-cell lymphoma, B-cell prolymphocytic leukaemia, lymphoplasmocytic lymphoma, mantle cell lymphoma, follicular lymphoma, marginal zone MALT-type lymphoma, lymph node marginal zone lymphoma with or without monocytoid B cells, splenic marginal zone lymphoma (with or without villous lymphocytes), tricholeucocytic leukaemia, diffuse large B-cell lymphoma, Burkitt's lymphoma, as well as any immune dysfunction diseases involving B lymphoid cells, including auto-immune diseases.

Another object of the invention is the use of the antibody according to the invention for the manufacture a drug for the treatment of lymphoid leukaemia.

Another object of the invention is the use of the antibody according to the invention for the manufacture of a drug for the treatment of B-type Chronic Lymphoid Leukaemia (B-CLL). Furthermore, the antibody according to the invention is particularly well suited for the treatment of conditions in which CD20 is less strongly expressed on B cells, and preferably, B-CLL (B-type Chronic Lymphocytic Leukaemia). In this regard, the antibody according to the invention may be used in combination with one or more further antibody(ies), e.g. monoclonal antibodies directed against one or more further antigens expressed on lymphoid cells, such as, for example, antigens HLA-DR, CD19, CD23, CD22, CD80, CD32 and CD52, for the manufacture of a drug for the treatment of leukaemia or lymphoma. Thus, the humanised antibody Campath-1H® (alentuzumab, MabCampathR®) which targets a molecule which is abundantly expressed on lymphoid cells, the CD52 antigen, and which induces cell lysis by mobilising the host effector mechanisms (complement binding, antibody-dependent cytotoxicity) is used in the treatment of CLL (Moreton P., Hillmen P. (2003) *Semin. Oncol.* 30(4): 493-501; Rawstron A. C. et al, (2004) *Blood* 103(6): 2027-2031; Robak T. (2004) *Leuk. Lymphoma* 45(2): 205-219; Stanglmaier M. et al, (2004) *Ann. Hematol.* 83(10): 634-645). Clinical tests are also underway to evaluate antibodies or immunotoxins which target the antigens HLA-DR, CD22, CD23, CD80 in patients with CLL (Mavromatis B. H., Cheson B. D. (2004) *Blood Rev.* 18(2): 137-148; Mavromatis B., Cheson B. D. (2003) *J. Clin. Oncol.* 21(9): 1874-1881, Coleman M. et al, (2003) *Clin. Cancer Res.* 9: 3991S-3994S; Salvatore G. et al, (2002) *Clin. Cancer Res.* 8: 995-1002).

In a further embodiment, the antibody according to the invention may be used in combination with cells which express FcγRs, such as NK cells, NKT (Natural Killers T) cells, Tγδ lymphocytes, macrophages, monocytes or dendritic cells, i.e. in combination with a cellular therapy (Peller S., Kaufman S. (1991) *Blood* 78: 1569, Platsoucas C. D. et al, (1982) *J. Immunol.* 129: 2305; Kimby E. et al, (1989) *Leukaemia* 3(7): 501-504; Soorskaar D. et al, *Int. Arch. Allery Appl. Immunol.* 87(2): 159-164; Ziegler H. W. et al, (1981) *Int. J. Cancer* 27(3): 321-327; Chaperot L. et al, (2000) *Leukaemia* 14(9): 1667-1677; Vuillier F., Dighiero G. (2003) *Bull. Cancer.* 90(8-9): 744-750).

In addition, the antibody according to the invention advantageously allows the doses administered to patients to be reduced: advantageously, the antibody dose administered to the patient is 2 times, 5 times, or even 10 times, 25 times, 50 times or particularly advantageously 100 times less than a dose of Rituxan®. Advantageously, the antibody dose administered to the patient is between 2 and 5 times, between 5 and 10 times, between 5 and 25 times, between 5 and 50 times, or even between 5 and 100 times less than a dose of Rituxan®. Thus, the antibody according to the invention, for instance the EMAB6 antibody, may advantageously be administered at a dose of less than 187.5 mg/m$^2$, 75 mg/m$^2$, 37.5 mg/m$^2$, 15 mg/m$^2$, 7.5 mg/m$^2$, or particularly advantageously less than 3.75 mg/m$^2$. The dose administered is advantageously between 187.5 mg/m$^2$ and 75 mg/m$^2$, or between 75 mg/m$^2$ and 37.5 mg/m$^2$, between 75 mg/m$^2$ and 15 mg/m$^2$, between 75 mg/m$^2$ and 7.5 mg/m$^2$, or even between 75 mg/m$^2$ and 3.75 mg/m$^2$.

Thus, the invention also refers to a method for treating diseases in which the target cells are cells which express CD20, such as malignant B-cell lymphoma, consisting in administering to a patient an effective dose of a composition containing an antibody according to the invention. More specifically, the treatment method is particularly suited to the treatment of leukaemia or lymphoma. Even more specifically, it is a method for treating a pathology chosen from acute B lymphoblastic leukaemia, B-cell lymphoma, mature B-cell lymphoma, including B-type Chronic Lymphocytic Leukaemia (B-CLL), small B-cell lymphoma, B-cell pro-lymphocytic leukaemia, lymphoplasmocytic lymphoma, mantle cell lymphoma, follicular lymphoma, marginal zone MALT-type lymphoma, lymph node marginal zone lymphoma with or without monocytoid B cells, splenic marginal zone lymphoma (with or without villous lymphocytes), tricholeucocytic leukaemia, diffuse large B-cell lymphoma, Burkitt's lymphoma, as well as any immune dysfunction diseases involving cells of the B lymphoid lines, including auto-immune diseases, consisting in administering an effective dosage of an antibody or antibody composition according to the invention.

A particular object of the invention is the use of an antibody according to the invention for the manufacture of a drug for the treatment of chronic graft-versus-host disease in order to treat symptoms which involve the receiver's B cells.

Finally, a last object of the invention is the use of an antibody according to the invention for the manufacture of a drug for a treatment of organ, in particular kidney, transplant rejection.

Recent studies (Ratanatharathorn et al, (August 2003) *Biol. Blood Marrow Transplant* 9(8): 505-511; Becker et al, (June 2004) *Am. J. Transplant.* 4(6): 996-1001) have in fact shown the benefits of anti-CD20 antibodies in the treatment of such conditions.

Further aspects and advantages of the invention will be described in the following examples which should be regarded as illustrative examples and do not limit the scope of the invention.

EXAMPLES

Example 1: Construction of Expression Vectors for Anti-CD20 Chimeric Antibodies EMAB6 and EMAB603

A. Determination of the Sequence of the Variable Regions of the CAT-13.6E12 Murine Antibody Total RNA from murine hybridoma CAT-13.6E12 cells (supplier: DSMZ, ref. ACC 474), which produces an IgG2a, κ-type immunoglobulin, was isolated (RNAeasy kit, Qiagen ref. 74104). After reverse transcription, the variable domains of the light (Vκ) and heavy (VH) chains of the CAT-13.6E12 antibody were amplified using the 5'RACE technique (Rapid Amplification of cDNA Ends) (GeneRacer kit, Invitrogen ref. L1500-01). The primers used for the two steps were the following:

1. Reverse Transcription Primers
a. Murine Kappa Specific Antisense Primer (SEQ ID No. 1)

```
5'-ACT GCC ATC AAT CTT CCA CTT GAC-3'
``` b. Murine G2a Specific Antisense Primer (SEQ ID No. 2)

```
5'-CTG AGG GTG TAG AGG TCA GAC TG-3'
```

2. 5'RACE PCR Primers
a. Murine Kappa Specific Antisense Primer (SEQ ID No. 3)

```
5'-TTGTTCAAGAAGCACACGACTGAGGCAC-3'
``` b. Murine G2a Specific Antisense Primer (SEQ ID No. 4)

```
5'-GAGTTCCAGGTCAAGGTCACTGGCTCAG-3'
```

The resulting VH and Vκ PCR products were cloned into vector pCR4Blunt-TOPO (Zero blunt TOPO PCR cloning kit, Invitrogen, ref. K2875-20) and sequenced. The nucleotide sequence of the Vκ region of the murine CAT-13.6E12 antibody is shown as sequence SEQ ID No. 5 and the deduced peptide sequence is sequence SEQ ID No. 6. The Vκ gene belongs to the Vκ4 class [Kabat et al. (1991) "Sequences of Proteins of Immunological Interest". NIH Publication 91-3242].

The nucleotide sequence of the VH region of CAT-13.6E12 is sequence SEQ ID No. 7 and the deduced peptide sequence is sequence SEQ ID No. 8. The VH gene belongs to the VH1 class [Kabat et al. (1991) "Sequences of Proteins of Immunological Interest". NIH Publication 91-3242].

B. Construction of Heavy and Light Chain Expression Vectors for Chimeric Antibodies EMAB6 and EMAB603

1. Light Chain Kappa Vector
1.1. Light Chain Vector for Antibody EMAB6

The Vκ sequence cloned into the pCR4Blunt-TOPO sequencing vector was amplified using the following cloning primers:
a) Vκ Sense Primer (SEQ ID No. 9)

```
5'-CTCAGTACTAGTGCCGCCACCATGGATTTTCAAGTGCAGATTTTC
AG-3'
```

The underlined sequence corresponds to the SpeI restriction site, the sequence in bold lettering corresponds to a Kozak consensus sequence, the ATG initiator is in italics.
b) Vκ Antisense Primer (SEQ ID No. 10)

```
5'-TGAAGACACTTGGTGCAGCCACAGTCCGGTTTATTTCCAGCCTGG
T-3'
```

This primer joins the murine Vκ sequences (in italics) to the human constant region (Cκ) (in bold). The underlined sequence corresponds to the DraIII restriction site.

Figure 1:
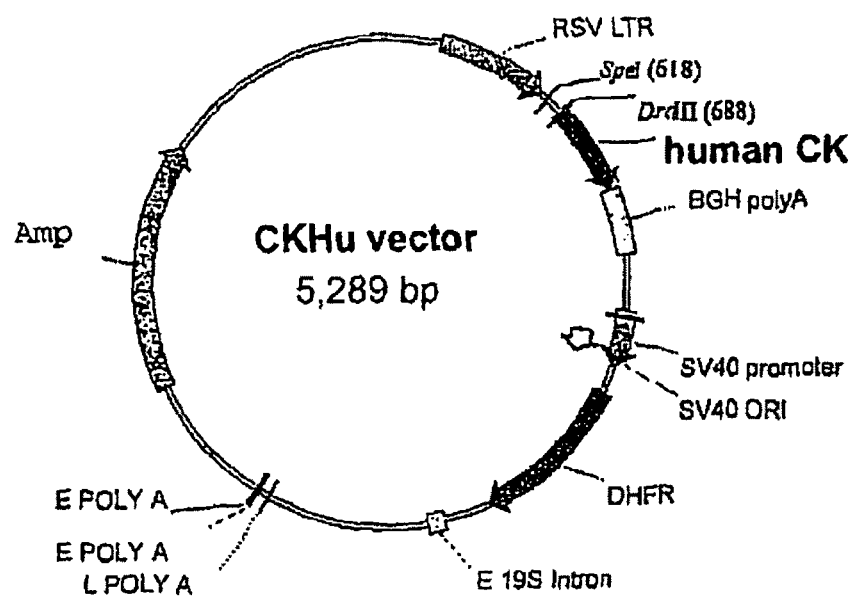
FIG. 1: Schematic representation of the CKHu vector used for the chimerisation of the light chain kappa of antibodies EMAB6 and EMAB603.

The resulting Vκ PCR product contains the sequence which codes for the natural signal peptide of the CAT-13.6E12 murine antibody. This Vκ PCR product was then cloned between the SpeI and DraIII sites of the light chain chimerisation vector (FIG. 1), which corresponds to sequence SEQ ID No. 11, at 5' in the human constant region Cκ, the nucleic acid sequence of which is sequence SEQ ID No. 21 and the deduced peptide sequence of which is sequence SEQ ID No. 22. The human Cκ sequence of this chimerisation vector had been modified beforehand by silent mutagenesis in order to create a DraIII restriction site to allow cloning of murine Vκ sequences to take place. This chimerisation vector contains an RSV promoter and a bGH (bovine Growth Hormone) polyadenylation sequence together with the dhfr (dihydrofolate reductase) selection gene.

The light chain sequence of the chimeric EMAB6 antibody encoded by this vector is shown as SEQ ID No. 13 for the nucleotide sequence and corresponds to the deduced peptide sequence SEQ ID No. 14.

1.2. Light Chain Vector for Antibody EMAB603

The protocol is the same as for the light chain vector for the EMAB6 antibody (see Example 1, B-1.1), apart from the Vκ antisense primer which is:
b') Vκ Antisense Primer (SEQ ID No. 29)

```
5'-TGAAGACACTTGGTGCAGCCACAGTCCGTTTTATTTCCA
GCCTGGT-3'
```

This primer joins the murine Vκ sequences (in italics) to the human constant region (Cκ) (in bold). The underlined sequence corresponds to the DraIII restriction site.

This primer also introduces the mutation AAC→AAA (framed nucleotide in the antisense primer sequence SEQ ID No. 29), which corresponds to mutation N106K (see nucleotide sequence and deduced peptide sequence SEQ ID No. 25 and SEQ ID No. 26) relative to the natural Vκ sequence of CAT-13.6E12 (see. SEQ ID No. 5 and SEQ ID No. 6).

The light chain sequence of the chimeric EMAB603 antibody encoded by this vector is shown as SEQ ID No. 27 for the nucleotide sequence and corresponds to the deduced peptide sequence SEQ ID No. 28.

2. Heavy Chain Vector

A similar approach was applied to the chimerisation of the heavy chains of the EMAB6 and EMAB603 antibodies.

The VH sequence cloned into the pCR4Blunt-TOPO vector was first of all amplified using the following cloning primers:

a) VH Sense Primer (SEQ ID No. 15)

5'-CTCAGTACTAGTGCCGCCACCATGGGATTCAGCAGGATCTTTCTC-3'

The underlined sequence corresponds to the restriction site SpeI, the sequence in bold lettering corresponds to a Kozak consensus sequence, the ATG initiator is in italics.

b) VH Antisense Primer (SEQ ID No. 16)

5'-GACCGATGGGCCCTTGGTGGAGGCTGAGGAGACGGTGACTGAGGTTCC-3'

This primer joins the murine VH sequences (in italics) to the human G1 constant region (in bold). The underlined sequence corresponds to the ApaI restriction site.

Figure 3:
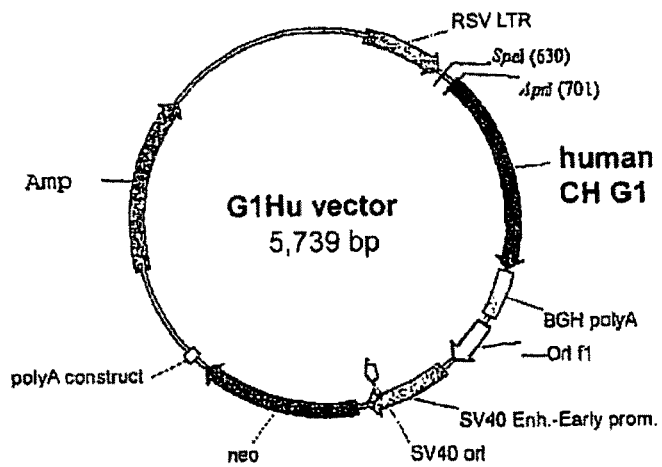
FIG. 3: Schematic representation of the G1Hu vector used for the chimerisation of the heavy chain of antibodies EMAB6 and EMAB603.

The amplified VH fragment contains the sequence which codes for the natural signal peptide of the CAT-13.6E12 murine antibody. This VH PCR product was then cloned between the SpeI and ApaI sites in the heavy chain chimerisation vector (FIG. 3) which corresponds to sequence SEQ ID No. 17, at 5' of the γ1 human constant region, the nucleic acid sequence of which is sequence SEQ ID No. 23 and the deduced peptide sequence of which is sequence SEQ ID No. 24. This chimerisation vector contains an RSV promoter and a bGH (bovine Growth Hormone) polyadenylation sequence as well as the neo selection gene.

The heavy chain sequences of the chimeric EMAB6 and EMAB603 antibodies encoded by this vector are shown as SEQ ID No. 19 for the nucleotide sequence and as SEQ ID No. 20 for the deduced peptide sequence.

3. Final Expression Vectors

3.1. EMAB6 Antibody Expression Vectors

Figure 2:
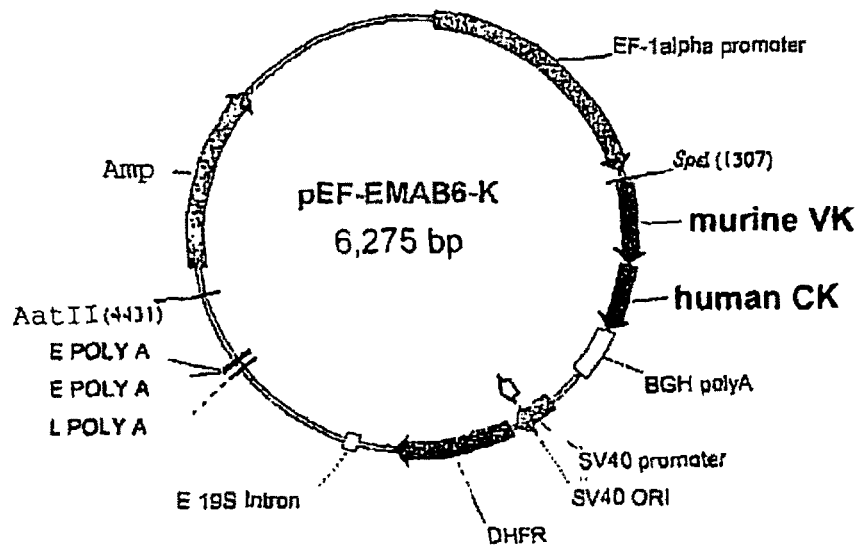
FIG. 2: Schematic representation of the light chain pEF-EMAB6-K expression vector used for the production of antibody EMAB6.

For the expression of the EMAB6 antibody, the RSV promoter of the kappa light chain chimerisation vector (see Example 1, B-1.1) was replaced with the human EF-1 alpha promoter. The final light chain pEF-EMAB6-K expression vector is shown in FIG. 2 and corresponds to sequence SEQ ID No. 12.

The light chain sequence of the chimeric EMAB6 antibody encoded by this vector is shown as SEQ ID No. 13 for the nucleotide sequence and corresponds to the deduced peptide sequence SEQ ID No. 14.

Figure 4:
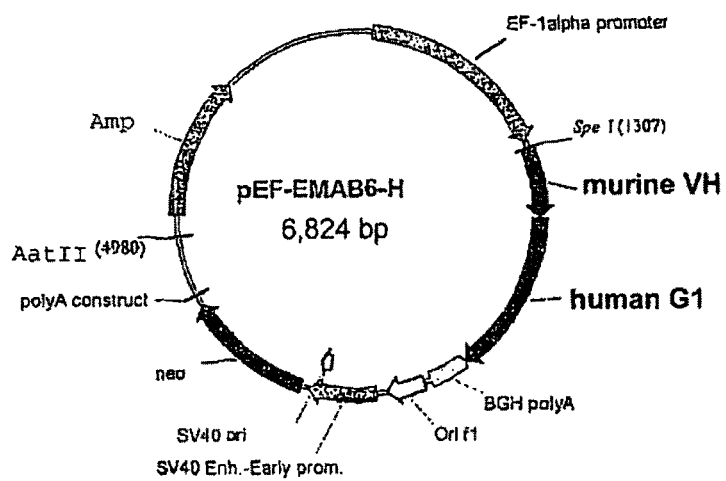
FIG. 4: Schematic representation of the heavy chain pEF-EMAB6-H expression vector used for the production of antibody EMAB6.

For the expression of the EMAB6 antibody, the RSV promoter of the heavy chain chimerisation vector (see Example 1, B-2) was replaced with the human EF-1 alpha promoter. The thus-obtained final heavy chain pEF-EMAB6-H expression vector is shown in FIG. 4 and corresponds to sequence SEQ ID No. 18.

3.2. EMAB603 Antibody Expression Vector

Figure 12:
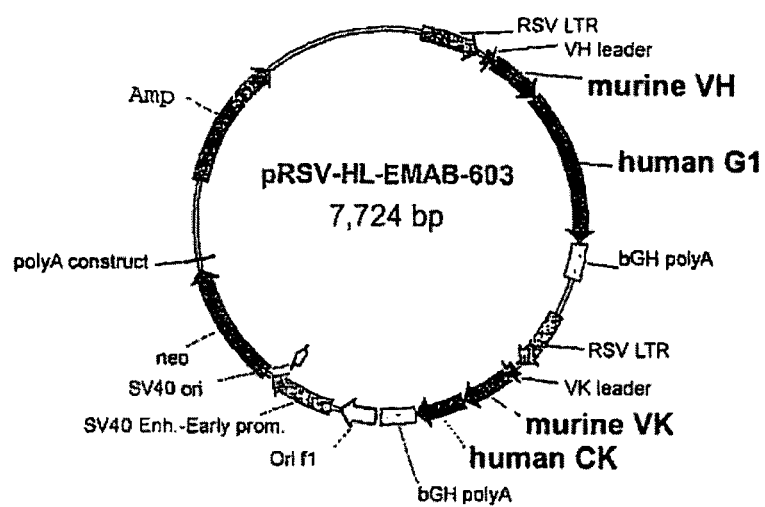
FIG. 12: Schematic representation of the heavy chain and light chain pRSV-HL-EMAB603 expression vector used for the production of antibody EMAB603.

A unique expression vector containing both heavy chain and light chain transcription units of the anti-CD20 EMAB603 antibody was constructed from two light and heavy chain chimerisation vectors (see Example 1, B-1.2 and B2 respectively) by sub-cloning into the XhoI site of the heavy chain vector, a BglII-PvuII fragment of the light chain vector containing the light chain transcription unit and the dhfr gene. This pRSV-HL-EMAB603 expression vector includes two selection genes, i.e. neo (neo-phosphotransferase II) and dhfr (dihydrofolate reductase), together with two heavy chain and light chain transcription units under the control of an RSV promoter (FIG. 12).

Example 2: Production of Cell Lines Derived from the YB2/0 Line Producing Anti-CD20 Chimeric EMAB6 and EMAB603 Antibodies The rat YB2/0 cell line (ATCC # CRL-1662) was cultivated in EMS medium (Invitrogen, ref. 041-95181M) containing 5% foetal calf serum (JRH Biosciences, ref. 12107). For transfection, 5 million cells were electroporated (Biorad electroporator, model 1652077) in Optimix medium (Equibio, ref. EKITE 1) with 25 µg of light chain vector pEF-EMAB6-K (FIG. 2), linearised with AatII, and 27 µg of heavy chain vector pEF-EMAB6-H (FIG. 4), linearised with ScaI, for the expression of the EMAB6 antibody, or with vector pRSV-HL-EMAB603, for the expression of the EMAB603 antibody. The electroporation conditions applied were 230 Volts and 960 microFarads in a 0.5-mL cuvette. Each electroporation cuvette was then distributed over 5 P96 plates at a density of 5,000 cells/well.

Placement in a selective RPMI medium (Invitrogen, ref 21875-034) containing 5% dialysed serum (Invitrogen, ref. 10603-017), 500 µg/mL G418 (Invitrogen, ref. 10131-027) and 25 nM methotrexate (Sigma, ref. M8407), was carried out 3 days after transfection.

The supernatants from the resistant transfection wells were screened for the presence of chimeric immunoglobulin (Ig) by applying an ELISA assay specific to the human Ig sequences.

The 10 transfectants producing the largest amount of antibody were amplified on P24 plates and their supernatants re-assayed using ELISA to estimate their productivity and select, by limited dilution (40 cells/plate), the best three producers for cloning.

After cloning, the R509.6A4 clone (R509-33903/046-6H1(1)6A4, productivity: 17 µg/$10^6$ cells), hereafter referred to as "R509", as well as the R603 clone were selected for the production of the chimeric EMAB6 and EMAB603 antibodies respectively and progressively acclimated to the CD Hybridoma production medium (Invitrogen, ref. 11279-023).

The production of the chimeric EMAB6 and EMAB603 antibodies was achieved by expanding, in CD Hybridoma medium, the acclimated culture obtained by dilution to 3×$10^5$ cells/mL in 75-cm$^2$ and 175-cm$^2$ vials and then dilution to 4.5×$10^5$ cells/mL in roller flasks. Once the maximum volume (1 L) was achieved, culture was continued until the cell viability was only 20%. After production, the chimeric EMAB6 and EMAB603 antibodies were purified using protein-A affinity chromatography (HPLC estimated purity <95%) and checked by polyacrylamide gel electrophoresis.

Example 3: Characterisation of the Functional Activity of Chimeric Antibodies EMAB6 and EMAB603

A. Specificity

Specificity of the antigen recognition of the chimeric EMAB6 antibody was evaluated by studying the competition with the murine antibody CAT-13.6E12 (CAT13) for binding the CD20 antigen expressed by Raji cells.

For that purpose, the EMAB6 antibody (10 µL at 0.5 to 50 µg/mL) was incubated at 4° C. with a fixed quantity of CAT-13.6E12 murine antibody (10 µL at 5 µg/mL) for 20 minutes in the presence of Raji cells (50 µL at 4×$10^6$ cells/mL). After washing, a mouse anti-IgG antibody coupled to phycoerythrin (PE) was added to the Raji cells so as to specifically detect the binding of the CAT-13.6E12 murine antibody. The Median Fluorescence Intensities (MFIs) obtained in the presence of various concentrations of EMAB6 are converted to percentages, with 100% corresponding to binding to CAT-13.6E12 cells in the absence of the EMAB6 antibody.

Figure 5:
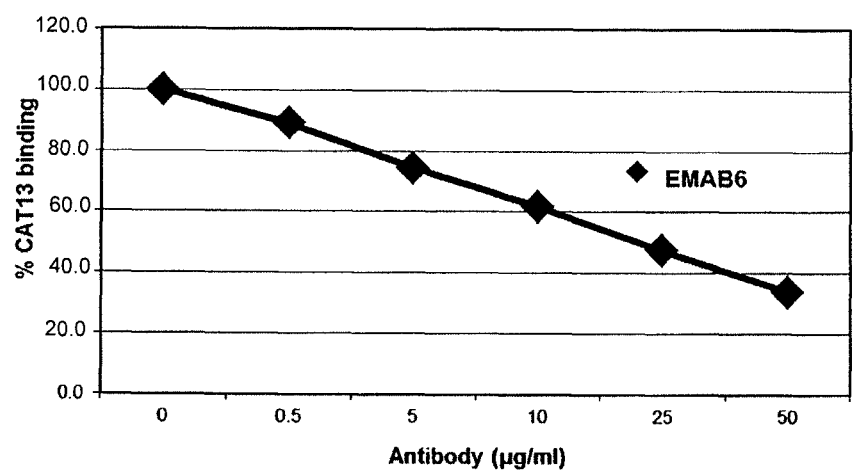
FIG. 5: Competition by the chimeric EMAB6 antibody for the binding of the murine antibody produced by CAT-13.6E12 (CAT13) to CD20 expressed on Raji cells.

An inhibition curve is thus obtained for binding of the CAT-13.6E12 (CAT13) antibody to Raji cells in the presence of increasing concentrations of EMAB6 (FIG. 5).

This study demonstrates that the chimerisation process has not adversely affected the specificity of the EMAB6 antibody, which does compete with the parental CAT-13.6E12 murine antibody for binding to CD20 expressed on the surface of Raji cells.

The antigen recognition specificity of the EMAB603 antibody is comparable with that of the EMAB6 antibody.

B. Complement-Dependent Cytotoxic Activity

Complement-dependent cytotoxic activity of the EMAB6 and EMAB603 antibodies was examined with Raji cells in the presence of young rabbit serum as a source of complement; the anti-CD20 chimeric antibody Rituxan® was included in one test, for comparison.

For this test, the Raji cells were adjusted to $6 \times 10^5$ cells/mL in IMDM (Iscove's Modified Dulbecco's Medium) 5% FCS (Foetal Calf Serum). The antibodies were diluted with IMDM+0.5% FCS. The reaction mixture was made up of 50 µL antibody, 50 µL young rabbit serum (1/10 IMDM+ 0.5% FCS dilution of Cedarlane CL 3441 reagent), 50 µL target cells and 50 µL IMDM+0.5% FCS medium. The final antibody concentrations were 5,000, 1,250, 250 and 50 ng/mL. A control without antibodies was included in the test. After 1 hr incubation at 37° C. in a 5% $CO_2$ atmosphere, the plates were centrifuged and the levels of intracellular LDH released into the supernatant estimated using a specific reagent (Cytotoxicity Detection Kit 1 644 793).

The percentage lysis was estimated using a calibration range obtained using various dilutions of target cells lysed using triton X100 (2%) corresponding to 100, 50, 25, and 0% lysis respectively.

Figure 6A:
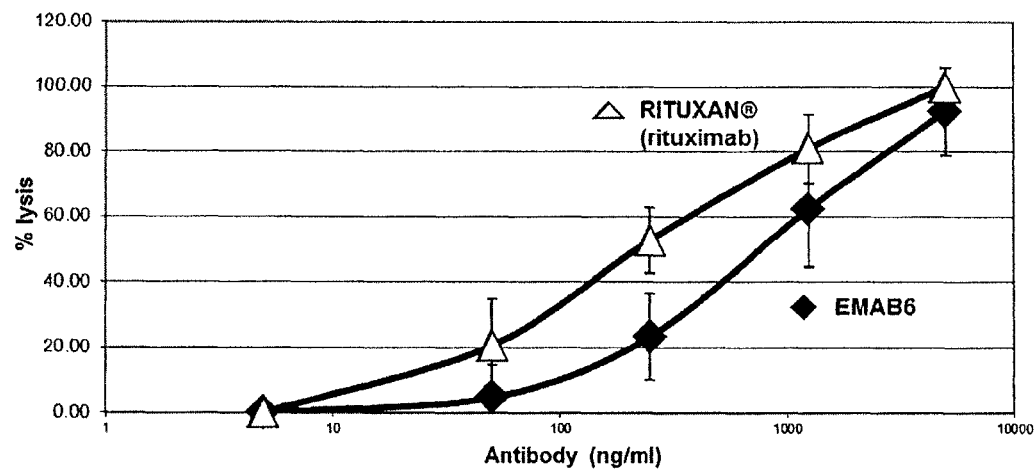
FIG. 6A: Complement-dependent cytotoxic activity of the anti-CD20 antibodies on Raji cells. Rituxan®: open triangle, EMAB6: closed lozenge. Cell lysis is estimated by measuring the intracellular LDH released into the supernatant. Results are expressed as percentage lysis, with 100% being the value obtained with Rituxan® (at 5,000 ng/mL anti-CD20 antibody). Mean of 5 tests.

The results shown in FIG. 6(A) demonstrate that EMAB6 and Rituxan® both induce complement-dependent lysis of the Raji cells. Nevertheless, EMAB6 complement activity appeared to be slightly less than that of Rituxan®. This difference is greater at the low concentrations of antibody used in this test. Thus for concentrations of 50 and 250 ng/mL, the activity of EMAB6 is of the order of 45% of that of Rituxan®. This difference becomes smaller as the antibody concentration is increased, with the % complement-dependent cytotoxic activity of the EMAB6 antibody representing 92% of that of Rituxan® at the highest concentration tested, i.e. 5,000 ng/mL.

This lower complement-dependent cytotoxic activity of the AMAB6 antibody compared to that of Rituxan® may be regarded as an advantage, since it limits the potential in vivo toxicity of EMAB6 compared to Rituxan®, associated with the activation of the conventional complement pathway, which leads to the production of various molecules with undesirable inflammatory, allergic and vascular activities.

Figure 6B:
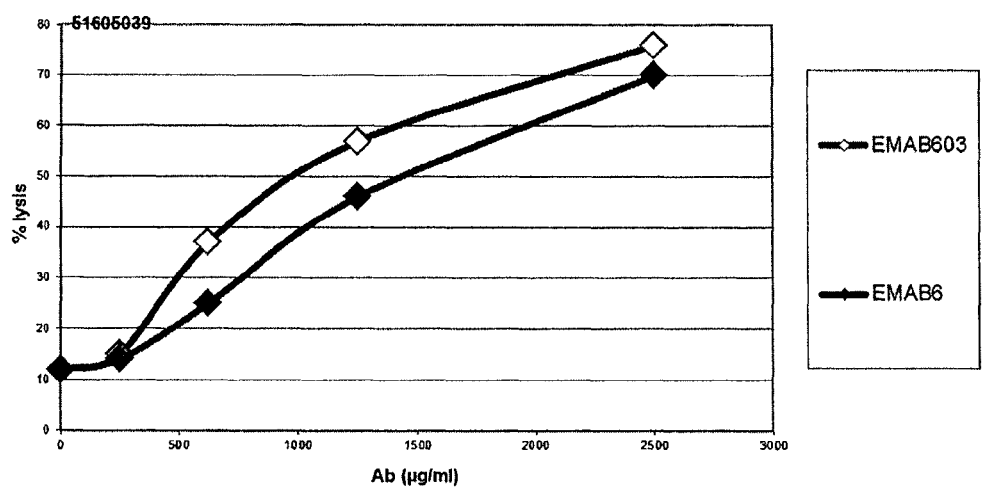
FIG. 6B: Complement-dependent cytotoxic activity of the anti-CD20 antibodies on Raji cells. Comparison of the complement-dependent cytotoxic activities of EMAB6 (closed lozenge) and EMAB603 (open lozenge).

The complement activity of the EMAB603 antibody is shown in FIG. 6(B).

C. ADCC Activity

The cytotoxicity of the chimeric EMAB6 antibody was evaluated in the presence of Raji cells or B lymphocytes from patients with CLL. The anti-CD20 chimeric antibody Rituxan® was included in the tests for comparison.

The calcein-labelling ADCC measurement technique used was as follows:

NK cells were isolated from PBMCs using the separation on magnetic beads (MACS) technique from Myltenyi. The cells were washed and re-suspended in IMDM+5% FCS ($45 \times 10^5$ cells/mL). The effector cells and target cells were used in a ratio of 15/1. The Raji cells or the PBMCs (Peripheral Blood Mononuclear Cells) from patients with B-CLL obtained after Ficoll treatment (>95% B cells) were labelled beforehand with calcein (1 mL cells at $3 \times 10^6$ cells/mL in IMDM+5% FCS+20 µL calcein (20 µM), 20 min incubation at 37° C. and then washing with HBSS (Hank's Buffered Saline Solution)) and adjusted to $3 \times 10^5$ cells/mL in IMDM+5% FCS. The antibodies were diluted with IMDM+ 0.5% FCS (final concentrations: 500; 50; 5; 0.5; 0.05 and 0.005 ng/mL).

The reaction mixture was made up of 50 µL antibody, 50 µL effector cells, 50 µL target cells and 50 µL IMDM medium in a P96 microtitration plate. Two negative controls were used:

Lysis without NK: NK effector cells were replaced with IMDM+5% FCS.

Lysis without antibodies (Ab): antibodies were replaced with IMDM+5% FCS.

After 4 hrs incubation at 37° C. in a 5% $CO_2$ atmosphere, the plates were centrifuged and the fluorescence associated with the supernatant was measured using a fluorimeter (excitation: 485 nm, emission: 535 nm).

The percentage lysis was estimated using a calibration range obtained using various dilutions of target cells lysed using Triton X100 (2%), corresponding to 100, 50, 25, and 0% lysis respectively.

The results were first calculated using the following formula:

% lysis=(% lysis with Antibody and NK)−(% lysis without Antibody)−(% lysis without NK)

and then expressed as relative percentages, with 100% being the value obtained at the highest concentration of Rituxan®.

Figure 7A:
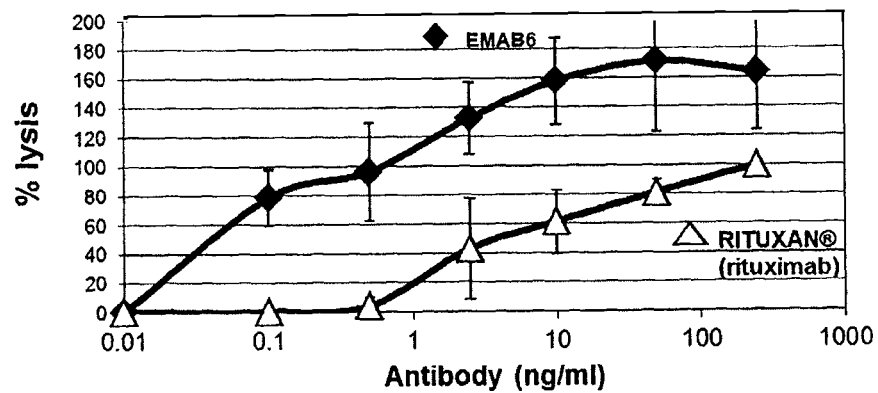
FIG. 7A: ADCC activity induced by anti-CD20 antibodies in the presence of Raji cells. Rituxan®: open triangle, EMAB6: closed lozenge. Cell lysis is estimated by measuring the intracellular LDH released into the supernatant. Results are expressed as percentage lysis, with 100% being the value obtained with Rituxan® (at 250 ng/mL anti-CD20 antibody). Mean of 3 tests.

The results obtained for the EMAB6 antibody on the Raji line cells shown in FIG. 7(A) demonstrate that, irrespective of the concentration being tested, the cytotoxicity induced by the EMAB6 antibody is greater than that induced by Rituxan®. This difference is particularly large at low antibody concentrations. Thus, at 0.5 ng/mL, the lysis percentages were 96% and 4% for EMAB6 and Rituxan® respectively. By increasing the dose 500-fold (250 ng/mL), the difference is still appreciable since the relative percentages of ADCC are 164% and 100% for EMAB6 and Rituxan® respectively. When the EC50s were calculated (antibody concentration corresponding to 50% of the E Max, the maximum effectiveness obtained at the highest antibody concentration and at the plateau) by graphical estimation (in ng/mL) and assuming that Rituxan® and EMAB6 attain the same E Max, the Rituxan® EC50/EMAB6 EC50 ratio in this test was then equal to 300.

Figure 7B:
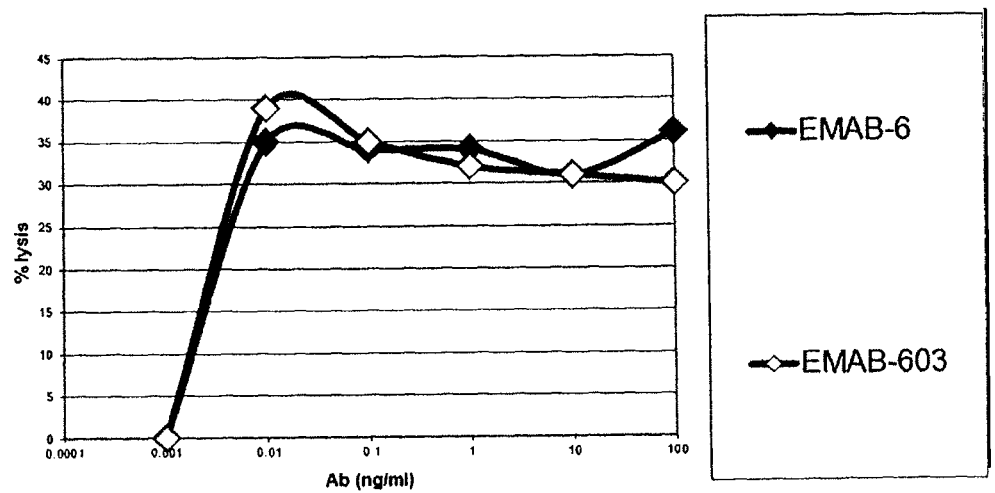
FIG. 7B: ADCC activity induced by anti-CD20 antibodies in the presence of Raji Cells. Comparison of ADCC induced by EMAB6 (closed lozenge) and EMAB603 (open lozenge).

The cytotoxicity of the chimeric EMAB603 antibody was evaluated in the presence of Raji cells using the same procedure as for the EMAB6 antibodies. Its activity was comparable with that of the EMAB6 antibody (see FIG. 7(B)).

Figure 8:
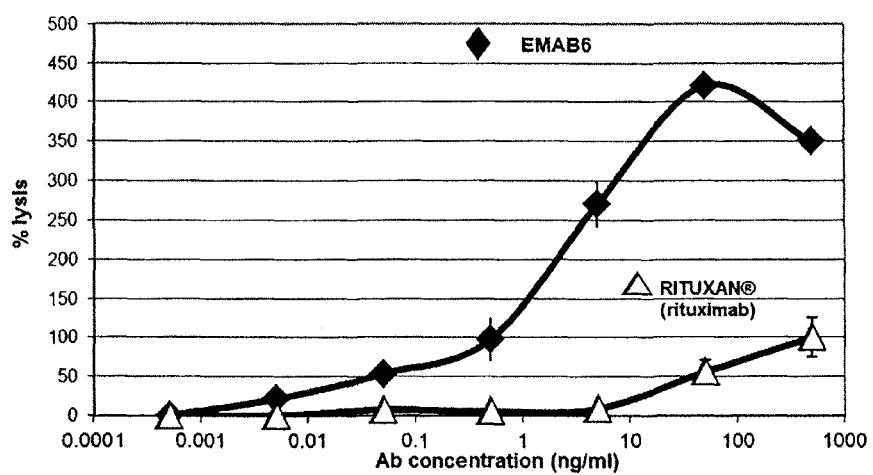
FIG. 8: ADCC activity induced by anti-CD20 antibodies in the presence of B lymphocytes from patients with B-CLL. Rituxan®: open triangle, EMAB6: closed lozenge. E/T ratio=15. Cell lysis is estimated by measuring the calcein released into the supernatant. Results are expressed as percentages, with 100% being the value obtained with Rituxan® (at 500 ng/mL anti-CD20 antibody). Mean of 4 experiments corresponding to 4 different patients.

With the lymphocytes from patients with B-CLL, the results obtained, shown in FIG. 8, demonstrate that, irrespective of the concentration being tested, the cytotoxicity induced by the EMAB6 antibody is greater than that induced by Rituxan®. As already observed with the Raji cells, this difference is particularly large at low antibody concentrations. A concentration of 0.5 ng/mL EMAB6 induces the same percentage lysis as 500 ng/mL Rituxan®, i.e. a concentration ratio of 1,000. At 5 ng/mL, the lysis percentages are 269% and 9% for EMAB6 and Rituxan® respectively. At the maximum dose tested (500 ng/mL), the difference is still very large since the relative percentages of ADCC are 350% and 100% for EMAB6 and Rituxan® respectively. An interesting result corresponds to the concentrations which give rise to 50% lysis. In this test, the Rituxan® EC50/EMAB6 EC50 ratio was estimated as 10,000 (graphical estimate in ng/mL for EC50 assuming that Rituxan® and EMAB6 attain the same E Max).

In these tests, the cytotoxic activities of EMAB6 and EMAB603 are therefore much greater than that of Rituxan®.

D. Activation of CD16 (IL-2 Secretion)

The activation of CD16 (FcγRIIIA) induced by the chimeric EMAB6 antibody was determined in the presence of Raji cells or B lymphocytes from patients with CLL. This test evaluated the ability of the antibody to bind to CD16 (FcγRIIIA) receptor expressed on the Jurkat-CD16 cells and to induce the secretion of IL-2. The anti-CD20 chimeric antibody Rituxan® is included in the tests for comparison.

Measurement of CD16 activation was carried out in the following manner on the Jurkat-CD16 cell line in the presence of Raji cells or B lymphocytes from patients with CLL.

Mixture in 96-well plate: 50 µL antibody solution (dilution to 10,000, 1,000, 100 and 10 ng/mL with IMDM+5% FCS for B lymphocytes from patients with B-CLL and 10,000, 2,000, 1,000, 200, 100, 50 and 25 ng/mL for Raji cells), 50 µL PMA (Phorbol Myristate Acetate, diluted to 40 ng/mL with IMDM+5% FCS), 50 µL Raji or PBMCs from patients with B-CLL obtained after Ficoll treatment (>95% B cells) diluted to $6 \times 10^5$/mL with IMDM+5% FCS, and 50 µL Jurkat-CD16 cells ($20 \times 10^6$/mL in IMDM+5% FCS). Controls without antibodies were included in all tests. After incubation overnight at 37° C., the plates were centrifuged and the IL-2 contained in the supernatants estimated using a commercial kit (Quantikine from R/D). The OD readings were made at 450 nm.

The results were initially expressed as IL-2 levels as a function of the antibody concentration (from 0 to 250 ng/mL final concentration), then as relative percentages, where 100% is the value obtained with Rituxan® at the highest test concentration.

Figure 9A:
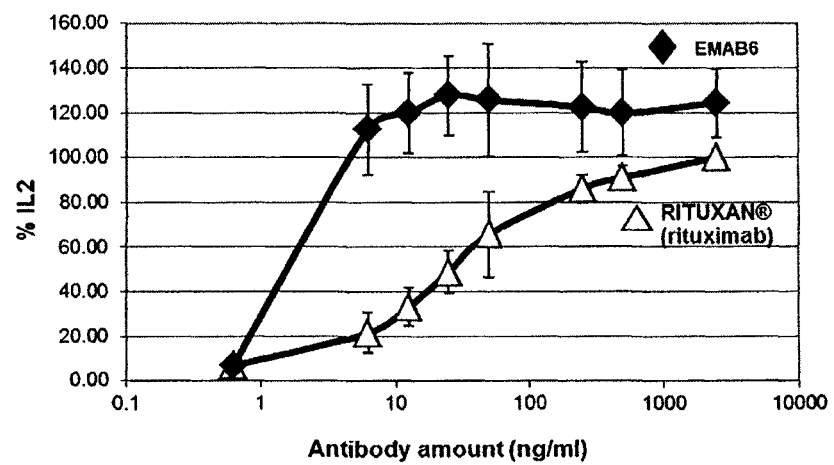
FIG. 9A: Activation of CD16 (FcγRIIIA) induced by anti-CD20 antibodies in the presence of Raji cells. Rituxan®: open triangle, EMAB6: closed lozenge. Results are expressed as percentage of IL-2, as measured in supernatants using ELISA; with 100% being the value obtained with Rituxan® (at 2,500 ng/mL anti-CD20 antibody). Mean of 4 tests.
Figure 9B:
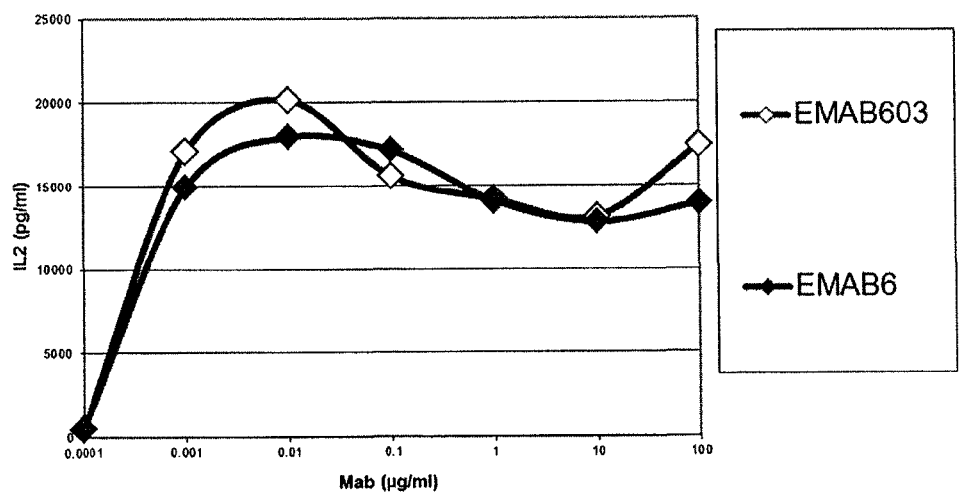
FIG. 9B: Activation of CD16 (Fcg RIIIA) induced by anti-CD20 antibodies in the presence of Raji cells. Comparison between the activation of CD16 (FcγRIIIA) as induced by EMAB6 (closed lozenge) and EMAB603 (open lozenge).

The results obtained with the Raji line cells shown in FIG. 9(A) demonstrate that, in the presence of EMAB6 and Rituxan®, the Jurkat-CD16 cells secrete IL-2, which indicates cell activation via binding of the Fc portion of the antibodies to CD16. The EMAB6 antibody, however, has an inductive activity which is much stronger than the Rituxan® antibody. Thus, at 6.25 ng/mL, the IL-2 percentages were 112% and 21% for EMAB6 and Rituxan® respectively. At 50 ng/mL, the difference is still large, with the percentages of IL-2 being 112% and 65% respectively. This difference decreases as concentration increases, with the respective percentages of IL-2 for EMAB6 and Rituxan® being 124% and 100% at 2,500 ng/mL. In this test, the Rituxan® EC50/EMAB6 EC50 ratio is estimated at 15 (graphical estimate in ng/mL for EC50 assuming that Rituxan® and EMAB6 attain the same E Max).

These results confirm the ADCC results, both being CD16-dependant. They demonstrate that the binding to CD16 (FcγRIIIA) by the Fc portion of the EMAB6 antibody is followed by a strong cellular activation which leads to the induction of effector functions.

The activation of CD16 (FcγRIIIA) induced by the chimeric EMAB603 antibody in the presence of Raji cells is comparable with that induced by the EMAB6 antibody.

Figure 10:
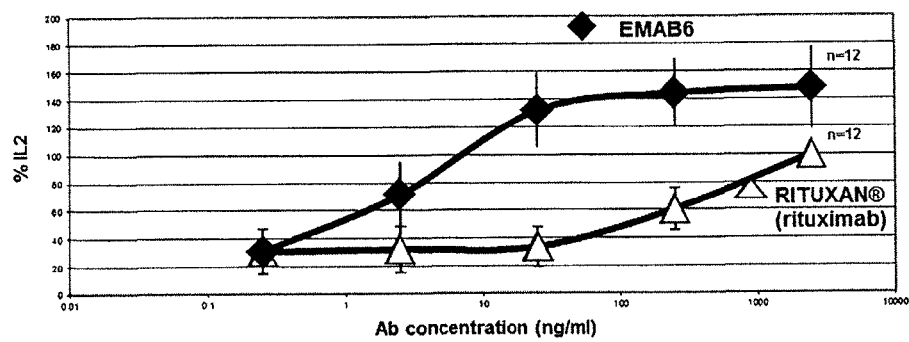
FIG. 10: Activation of CD16 (FcγRIIIA) induced by anti-CD20 antibodies in the presence of B lymphocytes from patients with B-CLL. Rituxan®: open triangle, EMAB6: closed lozenge. Results are expressed as percentage of IL-2, as measured in the supernatants using ELISA; with 100% being the value obtained with Rituxan® (at 2,500 ng/mL anti-CD20 antibody). Mean of 12 patients.
Figure 11:
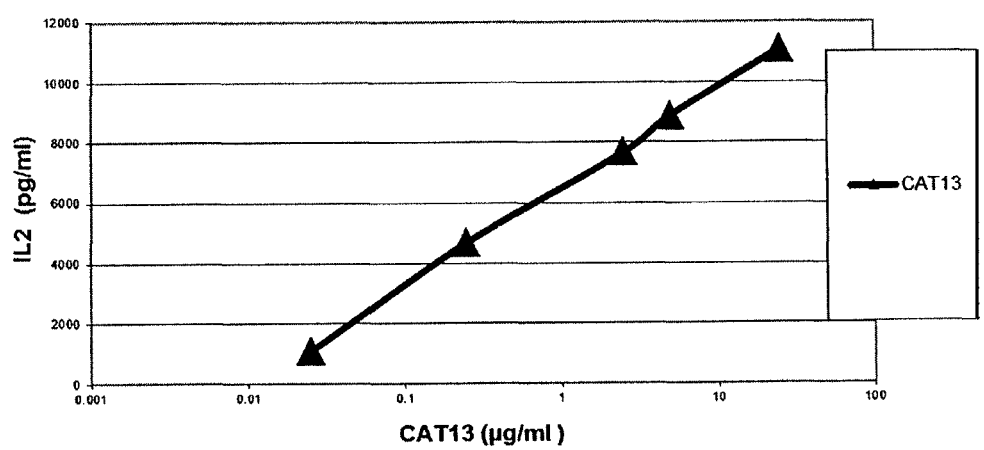
FIG. 11: Production of IL-2 induced by the CAT-13.6E12 murine antibody in the presence of Jurkat-CD16 cells (FcγRIIIA).

With lymphocytes from patients with B-CLL, the results obtained shown in FIG. 10 demonstrate that in the presence of anti-CD20 Rituxan® and EMAB6, the Jurkat-CD16 cells secrete IL-2, which indicates cell activation via binding of the Fc portion of the antibodies to CD16. The EMAB6 antibody, however, has an inductive ability which is much greater than the Rituxan® antibody. In fact, the IL-2 secretion induction activity of Rituxan® is close to the base line at concentrations of 2.5 and 25 ng/mL, whereas that of the EMAB6 antibody is significant. Thus at 25 ng/mL, the IL-2 percentages were 132% and 34% for EMAB6 and Rituxan® respectively. At the highest concentration (2,500 ng/mL), the IL-2 percentages were 148% and 100% respectively. The Rituxan® EC50/EMAB6 EC50 ratio in this test is greater than 100: it is estimated at 300 (graphical estimate in ng/mL for EC50 assuming that Rituxan® and EMAB6 attain the same E Max).

In conclusion, all the tests carried out on Raji cells demonstrate that the EMAB6 and EMAB603 antibodies, unlike Rituxan®, are highly cytotoxic and induce the activation of cells which express CD16 (FcγRIIIA), especially at low antibody concentrations. On the contrary, under the same conditions, the complement-dependent cytotoxic activity of EMAB6 decreases by about 50% compared to that of Rituxan®.

These results are confirmed by the studies carried out using cells isolated from patients with B-CLL, suggesting that the EMAB6 antibody is much more cytotoxic than Rituxan® towards B lymphocytes from patients with B-CLL. The differences between the two antibodies are more marked with lymphocytes from patients with B-CLL than with the Raji cells, which demonstrates the significant therapeutic interest of EMAB6 compared to Rituxan® for this condition.

The reason of this increased difference may be, amongst other, the lower antigen expression of CD20 on B lymphocytes from patients with B-CLL compared to Raji cells.

By analogy with Raji cells, it may be suggested that the complement-dependent cytotoxic activity of the EMAB6 antibody towards lymphocytes from patients with B-CLL must be less than that induced by Rituxan®, thus exhibiting the advantage of being less toxic in vivo as a result of the undesirable effects associated with a strong activation of the conventional complement pathway.

Example 4: Analysis of EMAB6 and EMAB603 Glycans by HPCE-LIF

The N-glycan structure of the heavy chains of the EMAB6 and EMAB603 antibodies was analysed using HPCE-LIF. The N-glycan structure of the heavy chain of Rituxan® was also analysed for comparison.

For that purpose, anti-CD20 monoclonal antibodies were desalted on a Sephadex G-25 column (HiTrap Desalting, Amersham Biosciences), evaporated and re-suspended in the hydrolysis buffer of PNGase F (Glyko) in the presence of 50 mM β-mercaptoethanol. After 16 hrs incubation at 37° C., the protein fraction was precipitated by adding absolute ethanol and the supernatant, which contained the N-glycans, was evaporated. The resulting oligosaccharides were either directly labelled using a fluorochrome: APTS (1-aminopyrene-3,6,8-trisulphonate), or subjected to the action of specific exoglycosidases before labelling with APTS. The resulting labelled oligosaccharides were injected onto an N-CHO capillary, separated and quantified by capillary electrophoresis with laser-induced fluorescence detection (HPCE-LIF).

The estimation of the fucose level was carried out either by the addition of the isolated fucosylated forms, or more specifically after the simultaneous action of neuraminidase, β-galactosidase and N-acetylhexosaminidase, which resulted in 2 peaks corresponding to the fucosylated or non-fucosylated pentasaccharide [GlcNac2-Man3] being obtained on the electrophoretogram:

TABLE 1

Analysis of anti-CD20 EMAB603 and Rituxan ® N-glycans

| Anti-CD20 | % Fucose | % Galactose | Fuc/Gal |
|---|---|---|---|
| EMAB603 | 15 | 37 | 0.4 |
| Rituxan ® | 93 | 57 | 1.63 |

The fucose level, expressed as %, was calculated using the following formula:

$$\text{Fucose level} = \frac{\text{fucosylated [GlcNac2-Man3]} \times 100}{[\text{GlcNac2-Man3} + \text{fucosylated GlcNac2-Man3}]}$$

The galactose level, expressed as %, was calculated by adding the percentages of the oligosaccharide forms containing galactose obtained after the action of neuraminidase and fucosidase. The formula used is as follows:

Galactose level=$(G1+G1B)+2x(G2+G2B)$

The fucose/galactose ratio is obtained by dividing the fucose level by the galactose level, calculated as described above.

From this analysis (see Table 1), it appears that the EMAB6 and EMAB603 antibodies are little fucosylated (% fucose<25%) compared to Rituxan® (% fucose=93%). In addition, the Fuc/Gal ratio (fucose/galactose ratio) for EMAB6 and EMAB603 is low (Fuc/Gal ratio<0.6), unlike the antibodies expressed in CHO cells such as Rituxan® (Fuc/Gal ratio=1.63).

The invention claimed is:

1. A method for the treatment of a disease in which the target cells are cells which express CD20, which comprises administering to a patient an effective amount of a monoclonal antibody directed against the CD20 antigen, wherein each of the light chains thereof has the murine-human chimeric amino acid sequence SEQ ID No. 28, and each of the heavy chains thereof has the murine-human chimeric amino acid sequence SEQ ID No. 20.

2. The method of claim 1, wherein the disease in which the target cells are cells which express CD20 is an immune dysfunction disease involving B lymphoid cells.

3. The method of claim 2, wherein the immune dysfunction disease involving B lymphoid cells is selected from auto-immune diseases.

4. The method of claim 1, wherein the disease in which the target cells are cells which express CD20 is chronic graft-versus-host disease.

5. The method of claim 1, wherein the disease in which the target cells are cells which express CD20 is organ transplant rejection.

6. The method of claim 5, wherein the organ transplant rejection is kidney transplant rejection.

7. The method of claim 1, wherein each of the light chains thereof is encoded by murine-human chimeric nucleic acid sequence SEQ ID No. 27, and each of the heavy chains thereof is encoded by murine-human chimeric nucleic acid sequence SEQ ID No. 19.

8. The method of claim 1, wherein the antibody is produced by a rat hybridoma cell line.

9. The method of claim 8, wherein the antibody is produced in the rat hybridoma cell line YB2/3HL.P2.G11.16Ag.20, registered at the American Type Culture Collection under ATCC number CRL-1662.

10. The method of claim 9, wherein the antibody is the EMAB603 antibody produced by clone R603, registered under registration number CNCM I-3529 at the Collection Nationale de Cultures de Microorganismes (CNCM).

11. The method of claim 1, wherein the antibody is produced in a CHO line.

12. A method for the treatment of a disease in which the target cells are cells which express CD20, which comprises administering to a patient an effective amount of a monoclonal antibody directed against the CD20 antigen and one or more further antibodies, wherein each of the light chains of the monoclonal antibody directed against the CD20 antigen has the murine-human chimeric amino acid sequence SEQ ID No. 28, and each of the heavy chains of the monoclonal antibody directed against the CD20 antigen has the murine-human chimeric amino acid sequence SEQ ID No. 20.

13. The method of claim 12, wherein the disease in which the target cells are cells which express CD20 is an immune dysfunction disease involving B lymphoid cells.

14. The method of claim 13, wherein the immune dysfunction disease involving B lymphoid cells is selected from auto-immune diseases.

15. The method of claim 12, wherein the disease in which the target cells are cells which express CD20 is chronic graft-versus-host disease.

16. The method of claim 12, wherein the disease in which the target cells are cells which express CD20 is organ transplant rejection.

17. The method of claim 16, wherein the organ transplant rejection is kidney transplant rejection.

* * * * *